US007785302B2

(12) United States Patent
Powers

(10) Patent No.: US 7,785,302 B2
(45) Date of Patent: Aug. 31, 2010

(54) ACCESS PORT IDENTIFICATION SYSTEMS AND METHODS

(75) Inventor: Kelly B. Powers, North Salt Lake, UT (US)

(73) Assignee: C. R. Bard, Inc., Murray Hill, NJ (US)

(*) Notice: Subject to any disclaimer, the term of this patent is extended or adjusted under 35 U.S.C. 154(b) by 1086 days.

(21) Appl. No.: 11/368,954

(22) Filed: Mar. 6, 2006

(65) Prior Publication Data
US 2006/0247584 A1 Nov. 2, 2006

Related U.S. Application Data

(60) Provisional application No. 60/658,518, filed on Mar. 4, 2005.

(51) Int. Cl.
*A61M 37/00* (2006.01)

(52) U.S. Cl. .................................................. 604/288.02

(58) Field of Classification Search ............ 604/288.01, 604/288.02
See application file for complete search history.

(56) References Cited

U.S. PATENT DOCUMENTS

| | | | |
|---|---|---|---|
| 574,387 A | 1/1897 | Buckler | |
| 611,357 A | 9/1898 | Dembinski | |
| 966,696 A | 8/1910 | Merrill | |
| 1,713,267 A | 5/1929 | Crowley | |
| 2,029,553 A | 2/1936 | Bartschi et al. | |
| 2,433,480 A | 12/1947 | Rendich | |
| 2,891,689 A | 6/1959 | Gould | |
| D198,453 S | 6/1964 | Weichselbaum | |
| 3,293,663 A | 12/1966 | Cronin | 623/8 |
| 3,341,417 A | 9/1967 | Sinaiko | 424/9.411 |
| 3,518,428 A | 6/1970 | Ring | |
| 3,529,633 A | 9/1970 | Vailancourt | |
| 3,643,358 A | 2/1972 | Morderosian | |
| 3,829,904 A | 8/1974 | Ling et al. | |
| 3,831,583 A | 8/1974 | Edmunds, Jr. et al. | 128/899 |
| 3,840,009 A | 10/1974 | Michaels et al. | |
| 3,891,997 A | 7/1975 | Herbert | |

(Continued)

FOREIGN PATENT DOCUMENTS

EP 0 619 101 A1 10/1994

(Continued)

OTHER PUBLICATIONS

MedComp "PortCT Technology", display at SIR Conference (Mar. 2006), Toronto, Canada.

(Continued)

*Primary Examiner*—Nicholas D Lucchesi
*Assistant Examiner*—Aarti B Berdichevsky
(74) *Attorney, Agent, or Firm*—Rutan & Tucker, LLP

(57) ABSTRACT

An access port for subcutaneous implantation is disclosed. Such an access port may comprise a body for capturing a septum for repeatedly inserting a needle therethrough into a cavity defined within the body. Further, the access port may include at least one feature structured and configured for identification of the access port subsequent to subcutaneous implantation. Methods of identifying a subcutaneously implanted access port are also disclosed. For example, a subcutaneously implanted access port may be provided and at least one feature of the subcutaneously implanted access port may be perceived. Further, the subcutaneously implanted access port may be identified in response to perceiving the at least one feature.

10 Claims, 30 Drawing Sheets

U.S. PATENT DOCUMENTS

| | | |
|---|---|---|
| 3,915,162 A | 10/1975 | Miller .................... 606/73 |
| 3,919,724 A | 11/1975 | Sanders et al. |
| 3,922,726 A | 12/1975 | Trentani et al. |
| 3,951,147 A | 4/1976 | Tucker et al. |
| 4,027,391 A | 6/1977 | Samis et al. |
| 4,035,653 A | 7/1977 | Karasko |
| 4,121,108 A | 10/1978 | Manor |
| 4,123,806 A | 11/1978 | Amstutz et al. |
| 4,168,586 A | 9/1979 | Samis |
| 4,190,040 A | 2/1980 | Schulte .................. 128/899 |
| 4,190,057 A | 2/1980 | Hill et al. |
| 4,194,122 A | 3/1980 | Mitchell et al. |
| 4,202,349 A | 5/1980 | Jones .................... 600/502 |
| 4,222,374 A | 9/1980 | Sampson et al. |
| 4,233,964 A | 11/1980 | Jefferts et al. |
| 4,274,006 A | 6/1981 | Caine |
| 4,349,498 A | 9/1982 | Ellis et al. |
| 4,361,153 A * | 11/1982 | Slocum et al. ............. 607/32 |
| 4,405,305 A | 9/1983 | Stephen et al. |
| 4,406,567 A | 9/1983 | Samis et al. |
| 4,425,119 A | 1/1984 | Berglund |
| 4,445,896 A | 5/1984 | Gianturco ................ 604/256 |
| 4,450,592 A | 5/1984 | Niederer et al. |
| 4,450,985 A | 5/1984 | Beard |
| 4,456,011 A | 6/1984 | Warnecke et al. |
| 4,469,483 A | 9/1984 | Becker et al. |
| 4,494,545 A * | 1/1985 | Slocum et al. ............. 607/32 |
| 4,506,676 A | 3/1985 | Duska |
| 4,529,635 A | 7/1985 | Sheldon |
| 4,543,088 A | 9/1985 | Bootman et al. ........ 604/288.02 |
| 4,549,879 A | 10/1985 | Groshong et al. |
| 4,559,046 A | 12/1985 | Groshong et al. |
| 4,571,749 A | 2/1986 | Fischell |
| 4,576,595 A | 3/1986 | Aas et al. ................ 604/256 |
| 4,612,877 A | 9/1986 | Hayes et al. |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam .................... 623/8 |
| 4,645,495 A | 2/1987 | Vaillancourt |
| 4,653,508 A * | 3/1987 | Cosman ................... 600/561 |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton et al. .............. 604/175 |
| 4,684,365 A | 8/1987 | Reinicke |
| 4,685,447 A | 8/1987 | Iversen et al. |
| 4,685,905 A | 8/1987 | Jeanneret nee Aab |
| 4,692,146 A | 9/1987 | Hilger |
| 4,695,273 A | 9/1987 | Brown .................... 604/173 |
| 4,697,595 A | 10/1987 | Breyer et al. |
| 4,701,166 A | 10/1987 | Groshong et al. |
| 4,704,103 A | 11/1987 | Stober et al. ............... 604/174 |
| 4,710,174 A | 12/1987 | Moden et al. |
| 4,718,894 A | 1/1988 | Lazorthes |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. ............ 604/175 |
| 4,767,410 A | 8/1988 | Moden et al. |
| 4,772,270 A | 9/1988 | Wiita et al. ............... 604/175 |
| 4,772,276 A | 9/1988 | Wiita et al. ............... 604/533 |
| 4,773,552 A | 9/1988 | Boege et al. |
| 4,778,452 A | 10/1988 | Moden et al. .......... 604/288.02 |
| 4,781,680 A | 11/1988 | Redmond et al. ...... 604/288.02 |
| 4,781,685 A | 11/1988 | Lehmann et al. |
| 4,781,695 A | 11/1988 | Dalton |
| 4,802,885 A | 2/1989 | Weeks et al. ........... 604/288.02 |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. ........ 604/288.02 |
| 4,848,346 A | 7/1989 | Crawford |
| 4,857,053 A | 8/1989 | Dalton .................. 604/288.02 |
| 4,861,341 A | 8/1989 | Woodburn |
| 4,863,470 A | 9/1989 | Carter ..................... 623/8 |
| 4,886,501 A | 12/1989 | Johnston et al. |
| 4,892,518 A | 1/1990 | Cupp et al. |
| 4,904,241 A | 2/1990 | Bark |
| 4,905,709 A | 3/1990 | Bieganski et al. |
| 4,909,250 A | 3/1990 | Smith |
| 4,915,690 A | 4/1990 | Cone et al. |
| 4,928,298 A | 5/1990 | Tanaka et al. |
| 4,929,236 A | 5/1990 | Sampson ................... 426/288 |
| 4,955,861 A | 9/1990 | Enegren et al. |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,009,644 A | 4/1991 | McDonald ................ 604/175 |
| 5,013,298 A | 5/1991 | Moden et al. |
| 5,041,098 A | 8/1991 | Loiterman et al. .......... 604/175 |
| 5,044,955 A | 9/1991 | Jagmin ..................... 433/229 |
| 5,045,060 A | 9/1991 | Melsky et al. .......... 604/288.02 |
| 5,045,064 A | 9/1991 | Idriss |
| 5,084,015 A | 1/1992 | Moriuchi ................ 604/288.02 |
| 5,085,216 A | 2/1992 | Henley, Jr. et al. |
| 5,090,066 A | 2/1992 | Schoepe et al. |
| 5,092,849 A | 3/1992 | Sampson .................. 604/175 |
| 5,108,317 A | 4/1992 | Beinhaur et al. |
| 5,108,377 A | 4/1992 | Cone et al. |
| 5,112,301 A | 5/1992 | Fenton, Jr. et al. |
| 5,112,303 A | 5/1992 | Pudenz et al. |
| 5,129,891 A | 7/1992 | Young |
| 5,137,529 A | 8/1992 | Watson et al. ............ 604/891.1 |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. ......... 604/116 |
| 5,167,633 A | 12/1992 | Mann et al. |
| 5,167,638 A | 12/1992 | Felix et al. |
| 5,171,228 A | 12/1992 | McDonald |
| 5,176,653 A | 1/1993 | Metals et al. |
| 5,176,662 A | 1/1993 | Bartholomew et al. |
| 5,178,612 A | 1/1993 | Fenton, Jr. |
| 5,185,003 A | 2/1993 | Brethauer ............. 604/288.02 |
| 5,189,690 A | 2/1993 | Samuel ..................... 378/162 |
| 5,193,106 A | 3/1993 | DeSena |
| 5,195,122 A | 3/1993 | Fabian ...................... 378/165 |
| 5,195,123 A | 3/1993 | Clement |
| 5,201,715 A | 4/1993 | Masters |
| 5,203,771 A | 4/1993 | Melker et al. |
| 5,203,777 A | 4/1993 | Lee ........................ 604/529 |
| 5,213,574 A | 5/1993 | Tucker ................ 604/288.02 |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,263,930 A | 11/1993 | Ensminger |
| 5,281,205 A | 1/1994 | McPherson ................ 604/267 |
| 5,290,263 A | 3/1994 | Wigness et al. |
| 5,295,658 A | 3/1994 | Atkinson et al. ........... 251/149.1 |
| 5,299,253 A | 3/1994 | Wessels |
| 5,309,863 A | 5/1994 | Leeb, Jr. |
| 5,312,337 A | 5/1994 | Flaherty et al. |
| 5,318,545 A | 6/1994 | Tucker ..................... 604/244 |
| 5,320,100 A | 6/1994 | Herweck et al. |
| 5,328,480 A | 7/1994 | Melker et al. |
| 5,332,398 A | 7/1994 | Miller et al. |

| Patent | Date | Inventor | Class |
|---|---|---|---|
| 5,336,194 A | 8/1994 | Polaschegg et al. | |
| 5,338,398 A | 8/1994 | Szwejkowski et al. | 438/720 |
| 5,350,360 A | 9/1994 | Ensminger et al. | |
| 5,352,204 A | 10/1994 | Ensminger | |
| 5,360,407 A | 11/1994 | Leonard | 604/175 |
| 5,383,223 A | 1/1995 | Inokuchi et al. | |
| 5,383,233 A | 1/1995 | Russell | 378/162 |
| 5,383,858 A | 1/1995 | Reilly et al. | |
| D355,240 S | 2/1995 | Gladfelter et al. | |
| 5,387,192 A | 2/1995 | Glantz et al. | 604/288.02 |
| 5,394,457 A | 2/1995 | Leibinger et al. | |
| 5,395,324 A | 3/1995 | Hinrichs et al. | |
| 5,397,329 A | 3/1995 | Allen | |
| 5,399,168 A | 3/1995 | Wadsworth, Jr. et al. | |
| 5,405,402 A | 4/1995 | Dye et al. | 623/22.38 |
| 5,417,565 A | 5/1995 | Long | |
| 5,417,656 A | 5/1995 | Ensminger et al. | |
| 5,421,814 A | 6/1995 | Geary | |
| 5,423,334 A | 6/1995 | Jordan | |
| 5,425,762 A | 6/1995 | Muller | |
| 5,456,698 A | 10/1995 | Byland et al. | |
| 5,476,460 A | 12/1995 | Montalvo | 604/891.1 |
| 5,476,880 A | 12/1995 | Cooke et al. | |
| 5,484,402 A | 1/1996 | Saravia et al. | |
| 5,503,630 A | 4/1996 | Ensminger et al. | |
| 5,507,813 A | 4/1996 | Dowd et al. | |
| 5,509,805 A | 4/1996 | Jagmin | 433/215 |
| 5,513,637 A | 5/1996 | Twiss et al. | |
| 5,514,103 A | 5/1996 | Srisathapat et al. | |
| 5,520,632 A | 5/1996 | Leveen et al. | |
| 5,527,277 A | 6/1996 | Ensminger et al. | |
| 5,527,307 A | 6/1996 | Srisathapat et al. | |
| 5,531,684 A | 7/1996 | Ensminger et al. | |
| 5,556,381 A | 9/1996 | Ensminger et al. | 604/288.03 |
| 5,558,641 A | 9/1996 | Glantz et al. | |
| 5,562,617 A | 10/1996 | Finch, Jr. et al. | |
| 5,562,618 A | 10/1996 | Cai et al. | |
| 5,575,770 A | 11/1996 | Melsky et al. | |
| 5,607,393 A | 3/1997 | Ensminger et al. | |
| 5,607,407 A | 3/1997 | Tolkoff et al. | |
| 5,613,945 A | 3/1997 | Cai et al. | |
| 5,620,419 A | 4/1997 | Lui et al. | 604/116 |
| 5,632,729 A | 5/1997 | Cai et al. | |
| 5,637,102 A | 6/1997 | Tolkoff et al. | 604/536 |
| 5,638,832 A | 6/1997 | Singer et al. | |
| 5,647,855 A | 7/1997 | Trooskin | |
| 5,662,612 A | 9/1997 | Niehoff | |
| 5,676,146 A | 10/1997 | Scarborough | 600/431 |
| 5,695,490 A | 12/1997 | Flaherty et al. | 604/891.1 |
| 5,702,128 A | 12/1997 | Maxim et al. | |
| 5,702,363 A | 12/1997 | Flaherty | |
| 5,704,915 A | 1/1998 | Melsky et al. | 604/175 |
| 5,709,668 A | 1/1998 | Wacks | |
| 5,713,844 A | 2/1998 | Peyman | |
| 5,713,858 A | 2/1998 | Heruth et al. | |
| 5,713,859 A | 2/1998 | Finch, Jr. et al. | |
| 5,718,382 A | 2/1998 | Jaeger | |
| 5,718,682 A | 2/1998 | Tucker | 604/288.02 |
| 5,725,507 A | 3/1998 | Petrick | |
| 5,733,336 A | 3/1998 | Neuenfeldt et al. | |
| 5,733,400 A | 3/1998 | Gore et al. | |
| 5,741,228 A | 4/1998 | Lambrecht et al. | |
| 5,743,873 A | 4/1998 | Cai et al. | |
| 5,743,891 A | 4/1998 | Tolkoff et al. | |
| 5,746,460 A | 5/1998 | Marohl et al. | |
| 5,758,667 A | 6/1998 | Slettenmark | |
| 5,769,823 A | 6/1998 | Otto | |
| 5,773,552 A | 6/1998 | Hutchings et al. | |
| 5,776,188 A | 7/1998 | Shepherd et al. | |
| 5,792,104 A | 8/1998 | Speckman et al. | 604/288.02 |
| 5,792,116 A | 8/1998 | Berg et al. | |
| 5,810,789 A | 9/1998 | Powers et al. | |
| 5,824,071 A | 10/1998 | Nelson et al. | |
| 5,830,172 A | 11/1998 | Leveen et al. | |
| 5,833,654 A | 11/1998 | Powers et al. | 604/93.01 |
| 5,835,563 A | 11/1998 | Navab et al. | |
| 5,836,935 A | 11/1998 | Ashton et al. | |
| 5,840,063 A | 11/1998 | Flaherty | |
| 5,843,069 A | 12/1998 | Butler et al. | 604/891.1 |
| 5,853,394 A | 12/1998 | Tolkoff et al. | |
| 5,868,702 A | 2/1999 | Stevens et al. | |
| 5,882,353 A | 3/1999 | VanBeek et al. | |
| 5,895,424 A | 4/1999 | Steele, Sr. et al. | |
| 5,906,596 A | 5/1999 | Tallarida | |
| 5,908,414 A | 6/1999 | Otto et al. | |
| 5,913,998 A | 6/1999 | Butler et al. | |
| 5,916,263 A | 6/1999 | Goicoechea et al. | |
| 5,925,017 A | 7/1999 | Kriesel et al. | |
| 5,925,030 A | 7/1999 | Gross et al. | |
| 5,928,197 A | 7/1999 | Niehoff | |
| 5,931,829 A | 8/1999 | Burbank et al. | 604/502 |
| 5,944,023 A | 8/1999 | Johnson et al. | |
| 5,944,688 A | 8/1999 | Lois | |
| 5,944,712 A | 8/1999 | Frassica et al. | 604/529 |
| 5,947,953 A | 9/1999 | Ash et al. | |
| 5,951,512 A | 9/1999 | Dalton | |
| 5,951,522 A | 9/1999 | Rosato et al. | |
| 5,954,687 A | 9/1999 | Baudino | |
| 5,957,890 A | 9/1999 | Mann et al. | |
| 5,968,011 A | 10/1999 | Larsen et al. | |
| 5,970,162 A | 10/1999 | Kawashima et al. | |
| 5,989,216 A | 11/1999 | Johnson et al. | |
| 5,989,239 A | 11/1999 | Finch et al. | 64/502 |
| 5,997,524 A | 12/1999 | Burbank et al. | |
| 6,007,516 A | 12/1999 | Burbank et al. | |
| 6,013,051 A | 1/2000 | Nelson | |
| 6,013,058 A | 1/2000 | Prosl et al. | |
| 6,017,331 A | 1/2000 | Watts et al. | |
| 6,022,335 A | 2/2000 | Ramadan | |
| 6,033,389 A | 3/2000 | Cornish | |
| 6,039,712 A | 3/2000 | Fogarty et al. | 604/288.02 |
| 6,077,756 A | 6/2000 | Lin et al. | |
| 6,086,555 A | 7/2000 | Eliasen | 604/93.01 |
| 6,090,066 A | 7/2000 | Schnell | 604/86 |
| 6,102,884 A | 8/2000 | Squitieri | |
| 6,113,572 A | 9/2000 | Gailey et al. | |
| 6,120,492 A | 9/2000 | Finch et al. | |
| 6,161,033 A | 12/2000 | Kuhn et al. | |
| 6,171,198 B1 | 1/2001 | Lizama Troncoso et al. | |
| 6,171,298 B1 | 1/2001 | Matsuura et al. | |
| 6,190,352 B1 | 2/2001 | Haarala et al. | |
| 6,193,684 B1 | 2/2001 | Burbank et al. | 604/29 |
| 6,198,807 B1 | 3/2001 | DeSena | |
| 6,203,570 B1 | 3/2001 | Baeke | |
| 6,213,973 B1 | 4/2001 | Eliasen et al. | 604/93.01 |
| 6,228,088 B1 | 5/2001 | Miller et al. | |
| 6,251,059 B1 | 6/2001 | Apple et al. | |
| D445,175 S | 7/2001 | Bertheas | |
| 6,269,148 B1 | 7/2001 | Jessop et al. | |
| 6,287,293 B1 | 9/2001 | Jones et al. | 604/891.1 |
| 6,290,677 B1 | 9/2001 | Arai et al. | |
| 6,305,413 B1 | 10/2001 | Fischer et al. | |
| D450,115 S | 11/2001 | Bertheas | |
| 6,332,874 B1 | 12/2001 | Eliasen et al. | |
| 6,355,021 B1 | 3/2002 | Nielsen et al. | |
| 6,356,782 B1 | 3/2002 | Sirimanne et al. | 600/431 |
| 6,361,557 B1 | 3/2002 | Gittings et al. | |
| 6,398,764 B1 | 6/2002 | Finch, Jr. et al. | |
| 6,419,680 B1 | 7/2002 | Cosman et al. | |
| 6,450,937 B1 | 9/2002 | Mercereau et al. | |
| 6,478,783 B1 | 11/2002 | Moorehead | |
| 6,482,217 B1 | 11/2002 | Pintor et al. | |
| 6,494,867 B1 | 12/2002 | Elver et al. | |
| 6,497,062 B1 | 12/2002 | Koopman et al. | |
| 6,500,155 B2 | 12/2002 | Sasso | |
| 6,503,228 B1 * | 1/2003 | Li et al. | 604/175 |

| | | |
|---|---|---|
| 6,527,754 B1 | 3/2003 | Tallarida et al. ........ 604/288.04 |
| 6,537,255 B1 | 3/2003 | Raines |
| RE38,074 E | 4/2003 | Recinella et al. |
| 6,582,418 B1 | 6/2003 | Verbeck et al. |
| 6,613,002 B1 | 9/2003 | Clark et al. |
| 6,613,662 B2 | 9/2003 | Wark et al. |
| 6,626,936 B2 | 9/2003 | Stinson |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,676,633 B2 | 1/2004 | Smith et al. |
| 6,697,664 B2 | 2/2004 | Kienzle III et al. |
| 6,705,316 B2 | 3/2004 | Blythe et al. |
| 6,719,721 B1 | 4/2004 | Okazaki et al. |
| 6,719,739 B1 | 4/2004 | Verbeek et al. |
| 6,738,531 B1 | 5/2004 | Funahashi et al. |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,826,257 B2 | 11/2004 | Sayre et al. |
| 6,852,106 B2 | 2/2005 | Watson et al. |
| 6,878,136 B2 | 4/2005 | Fleury et al. |
| 6,878,137 B2 | 4/2005 | Benchetrit |
| 6,949,084 B2 | 9/2005 | Marggi et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie, Jr. et al. |
| 7,044,942 B2 | 5/2006 | Jolly et al. |
| 7,056,316 B1 | 6/2006 | Burbank et al. |
| 7,070,591 B2 | 7/2006 | Adams et al. |
| 7,072,704 B2 | 7/2006 | Bucholz ..................... 600/407 |
| 7,074,232 B2 | 7/2006 | Kanner et al. |
| 7,083,593 B2 | 8/2006 | Stultz |
| 7,108,686 B2 | 9/2006 | Burke et al. |
| 7,123,690 B1 | 10/2006 | Brown et al. |
| 7,127,040 B2 | 10/2006 | Sayre et al. |
| 7,131,962 B1 | 11/2006 | Estabrook et al. |
| 7,140,769 B2 | 11/2006 | Kay |
| 7,191,011 B2 | 3/2007 | Cantlon ....................... 607/60 |
| 7,198,631 B2 | 4/2007 | Kanner et al. |
| 7,214,207 B2 | 5/2007 | Lynch et al. |
| 7,214,215 B2 | 5/2007 | Heinzerling et al. |
| 7,223,257 B2 | 5/2007 | Shubayev et al. |
| 7,229,417 B2 | 6/2007 | Foerster et al. |
| 7,235,067 B2 | 6/2007 | Morris et al. |
| D546,440 S | 7/2007 | Burnside |
| 7,242,982 B2 | 7/2007 | Singhal et al. |
| 7,252,469 B2 | 8/2007 | Zaluzec et al. |
| 7,252,649 B2 | 8/2007 | Sherry ..................... 604/93.01 |
| 7,261,705 B2 | 8/2007 | Edoga et al. ................. 524/544 |
| D554,253 S | 10/2007 | Kornerup et al. |
| 7,275,682 B2 | 10/2007 | Excoffier et al. |
| 7,276,075 B1 | 10/2007 | Callas et al. |
| D556,153 S | 11/2007 | Burnside |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,443 S | 2/2008 | Zinn et al. |
| 7,331,130 B2 | 2/2008 | Schweikert |
| 7,331,948 B2 | 2/2008 | Skarda |
| 7,333,013 B2 * | 2/2008 | Berger ................... 340/539.12 |
| D564,449 S | 3/2008 | Dewberry |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| D595,892 S | 7/2009 | Smith et al. |
| 7,563,025 B2 | 7/2009 | Kay |
| 7,713,251 B2 | 5/2010 | Tallarida et al. |
| 2001/0016717 A1 | 8/2001 | Haarala et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. ........ 604/288.02 |
| 2002/0095205 A1 | 7/2002 | Edwin et al. |
| 2002/0138068 A1 | 9/2002 | Watson et al. |
| 2002/0173769 A1 | 11/2002 | Gray et al. |
| 2003/0028173 A1 | 2/2003 | Forsberg |
| 2003/0130627 A1 | 7/2003 | Smith et al. |
| 2003/0139812 A1 | 7/2003 | Garcia et al. |
| 2003/0181878 A1 | 9/2003 | Tallarida et al. |
| 2003/0191452 A1 | 10/2003 | Meglin et al. |
| 2004/0020462 A1 | 2/2004 | Sauler et al. |
| 2004/0044306 A1 | 3/2004 | Lynch et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0073196 A1 | 4/2004 | Adams et al. |
| 2004/0106878 A1 | 6/2004 | Skujins et al. |
| 2004/0106891 A1 | 6/2004 | Langan et al. |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0199129 A1 | 10/2004 | DiMatteo |
| 2004/0199220 A1 | 10/2004 | Cantlon |
| 2004/0204692 A1 | 10/2004 | Eliasen |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0049553 A1 | 3/2005 | Triplett et al. |
| 2005/0070875 A1 | 3/2005 | Kulessa |
| 2005/0075614 A1 | 4/2005 | Bunodiere et al. ..... 604/288.02 |
| 2005/0113806 A1 | 5/2005 | Murphree et al. ........ 604/890.1 |
| 2005/0131352 A1 | 6/2005 | Conlon et al. |
| 2005/0148866 A1 | 7/2005 | Gunderson |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong ........................... 710/1 |
| 2005/0209573 A1 | 9/2005 | Brugger et al. |
| 2005/0215874 A1 | 9/2005 | Wang et al. .................. 600/407 |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0116648 A1 | 6/2006 | Hamatake |
| 2006/0173410 A1 | 8/2006 | Moberg et al. |
| 2006/0173424 A1 | 8/2006 | Conlon |
| 2006/0178647 A1 | 8/2006 | Stats |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton ..................... 604/93.01 |
| 2006/0224128 A1 | 10/2006 | Lurvey et al. |
| 2006/0224129 A1 | 10/2006 | Beasley et al. |

| | | |
|---|---|---|
| 2006/0247584 A1 | 11/2006 | Sheetz et al. |
| 2006/0253076 A1 | 11/2006 | Butts et al. |
| 2006/0264898 A1 | 11/2006 | Beasley et al. |
| 2007/0007839 A1 | 1/2007 | Lin |
| 2007/0049876 A1 | 3/2007 | Patton .................. 604/288.01 |
| 2007/0055290 A1 | 3/2007 | Lober |
| 2007/0073250 A1 | 3/2007 | Schneiter ............... 604/288.01 |
| 2007/0078391 A1 | 4/2007 | Wortley et al. .............. 604/116 |
| 2007/0078416 A1 | 4/2007 | Eliasen .................. 604/288.02 |
| 2007/0078432 A1 | 4/2007 | Halseth et al. ............. 604/500 |
| 2007/0083156 A1 | 4/2007 | Muto et al. .............. 604/93.01 |
| 2007/0149920 A1 | 6/2007 | Michels et al. |
| 2007/0149921 A1 | 6/2007 | Michels et al. |
| 2007/0161958 A1 | 7/2007 | Glenn ........................ 604/175 |
| 2007/0179456 A1 | 8/2007 | Glenn |
| 2007/0185462 A1 | 8/2007 | Byrum .................. 604/288.02 |
| 2007/0191773 A1 | 8/2007 | Wojcik |
| 2007/0208313 A1 | 9/2007 | Conlon et al. |
| 2007/0219510 A1 | 9/2007 | Zinn et al. |
| 2007/0233017 A1 | 10/2007 | Zinn et al. ............. 604/288.01 |
| 2007/0233018 A1 | 10/2007 | Bizup et al. ............ 604/288.01 |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0299408 A1 | 12/2007 | Alferness et al. |
| 2008/0004642 A1 | 1/2008 | Birk et al. .................... 606/157 |
| 2008/0008654 A1 | 1/2008 | Clarke et al. |
| 2008/0015701 A1 | 1/2008 | Garcia et al. |
| 2008/0039820 A1 | 2/2008 | Sommers et al. |
| 2008/0048855 A1 | 2/2008 | Berger |
| 2008/0114308 A1 | 5/2008 | di Palma et al. |
| 2008/0138387 A1 | 6/2008 | Machiraju |
| 2008/0140025 A1 | 6/2008 | Sheetz et al. |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118683 A1 | 5/2009 | Hanson et al. |
| 2009/0156928 A1 | 6/2009 | Evans et al. |
| 2009/0204072 A1 | 8/2009 | Amin et al. |
| 2009/0204074 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2010/0042073 A1 | 2/2010 | Oster et al. |
| 2010/0069743 A1 | 3/2010 | Sheetz et al. |

FOREIGN PATENT DOCUMENTS

| | | |
|---|---|---|
| EP | 2006019101 A2 | 12/2006 |
| JP | 2006025948 A | 2/2006 |
| WO | WO-8600213 | 1/1986 |
| WO | 9305730 A1 | 4/1993 |
| WO | WO097/01370 | 1/1997 |
| WO | 9706845 A1 | 2/1997 |
| WO | 9817337 A1 | 4/1998 |
| WO | WO99/42166 | 8/1999 |
| WO | 0033901 A1 | 6/2000 |
| WO | WO-02/47549 | 6/2002 |
| WO | WO-0247549 | 6/2002 |
| WO | WO 2004/004800 A2 | 1/2004 |
| WO | 2004071555 A2 | 8/2004 |
| WO | 2004091434 A2 | 10/2004 |
| WO | 2005037055 A2 | 4/2005 |
| WO | 2006078915 A2 | 7/2006 |
| WO | 2006096686 A1 | 9/2006 |
| WO | 2006116438 A2 | 11/2006 |
| WO | 2006130133 A1 | 12/2006 |
| WO | 2006134100 A1 | 12/2006 |
| WO | WO-2007079024 A2 | 7/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | WO2007/136538 | 11/2007 |
| WO | WO 2008/008126 A2 | 1/2008 |
| WO | WO 2008/019236 A1 | 2/2008 |
| WO | WO-2008048361 | 4/2008 |
| WO | WO-2008/063226 | 5/2008 |
| WO | 2008147760 A1 | 12/2008 |
| WO | 2009002839 A1 | 12/2008 |
| WO | WO-2008/157763 | 12/2008 |
| WO | WO-2009/012385 | 1/2009 |
| WO | WO-2009/012395 | 1/2009 |
| WO | WO-2009/035582 | 3/2009 |
| WO | 2009046725 A1 | 4/2009 |
| WO | WO-2009/046439 | 4/2009 |
| WO | 2009108669 A1 | 9/2009 |

OTHER PUBLICATIONS

Cardiovascular and Interventional Radiology, Review Article, "Central Venous Access Catheters: Radiological Management of Complications," by U.K. Teichgraber, B. Gebauer, T. Benter, and H.J. Wagner, published online Jul. 31, 2003.

International Search Report and Written Opinion, dated Oct. 1, 2007, from PCT/US06/49007, filed Dec. 21, 2006.

European Patent Office Communication, dated Mar. 1, 2005, for Application No. 99 964 086.5-1257, Applicant STD Manufacturing, Inc.

European Patent Office communication, dated Mar. 30, 2005, for Application No. 99 964 086.5-1257, Applicant STD Manufacturing, Inc.

European Patent Office communication, dated Dec. 15, 2005, for Application No. 99 964 086.5-1257, Applicant STD Manufacturing, Inc.

Partial International Search Report dated Sep. 29, 2006 from related Patent Cooperation Treaty Application No. PCT/US2006/015695.

European Patent Office communication, dated Sep. 2, 2008, for Application No. 06 751 411.7-1526, Applicant C.R. Bard, Inc.

Non-Final Office Action issued on Feb. 13, 2008, in U.S. Appl. No. 11/320,223, filed Dec. 28, 2005.

Non-Final Office Action issued on Sep. 18, 2008, in U.S. Appl. No. 11/320,223, filed Dec. 28, 2005.

Non-Final Office Action issued on Jan. 16, 2009, in U.S. Appl. No. 11/380,124, filed Apr. 25, 2006.

International Search Report from related International Application No. PCT/US2006/008022, dated Jul. 5, 2006.

Nucleus Cochlear Implant Systems; User Manual for the ESPrit 3G speech processor and accessories, Issue 2, Dec. 2001 http://www.cochlearamericas.com/PDFs/UserManualSprint.pdf.

BARD Access System product drawings representative of the BARD Access System products on the market on or around Mar. 1995 as indicated by the BARD Access Systems Mar. 21, 1995 Product Release to Market form for "M.R.I. Port with 8 Fr. ChronoFlex® Catheter," "M.R.I. Port with 8Fr. ChronoFlex Catheter with Intro-Eze™," "M.R.I. Port with 8. Fr ChronoFlex Catheter and Peel Apart," "M.R.I. Port with 8Fr. ChronoFlex Catheter Demo Kit." Product drawings included.

BioEnterics® LAP-BAND® "Adjustable Gastric Banding System" by Inamed Health. Product Brochure. Dec. 2003.

LaMaitre Vascular "Port Implantations: using the OptiLock Implantable Port" product information, http://www.lemaitre.com/specs_pop.asp. Apr. 2003.

LAP-BAND AP™ "System with Adjustable Gastric Banding System with OMNIFORM™ Design" Product Brochure. Jul. 2007.

LAP-BAND® "Adjustable Gastric Banding System" by BioEnterics Corporation. Product Brochure.

LAP-BAND® System Fact Sheet. © 2007 Allergan, Inc.

Oct. 22, 2009 Declaration of Kelly Christian, Director of Product Development at BARD Access Systems, Inc. in support of and depicting a product on the market by Quinton Company approximately ten years ago.

PORT-A CATH® "Implantable Epidural, Aterial and Peritonial Access Systems" Internet Product Listing. http://web.archive.org/web/20001119035900/www.deltec.com/cPacspl.htm. Printed Oct. 17, 2009.

PORT-A-CATH® "Many PORT-A-CATH® System Choices" Product Brochure. © 1996 SIMS Deltec, Inc.

PORT-A-CATH® "Single-lumen Implantable Vascular Access Systems" Product Specifications. 2004 Smith Medical family of companies.

Rappolt, Richard T., et al. "Radiopaque Codification and X-ray Identification of Ingested Drugs." Ingestive Radiology, May-Jun. 1966.

Shah, Tilak M., "Radiopaque Polymer Formulations for Medical Devices." Medical Device and Diagnostic Industry, Mar. 2000.

Urquiola, Javier, et al., "Using Lead Foil as a Radiopaque Marker for Computerized Tomography Imaging When Implant Treatment Planning." The Journal of Prosthetic Dentistry, 1997.

U.S. Appl. No. 10/374,000, filed Feb. 25, 2003 Response to Office Action dated Dec. 28, 2006.

U.S. Appl. No. 10/374,000, filed Feb. 25, 2003 Response to Office Action dated Jun. 20, 2008.

U.S. Appl. No. 10/374,000, filed Feb. 25, 2003 Response to Office Action dated Mar. 30, 2009.

U.S. Appl. No. 10/374,000, filed Feb. 25, 2003 Response to Office Action dated Sep. 21, 2009.

U.S. Appl. No. 10/374,000, filed Feb. 25, 2003; non-final Office Action, mailed May 20, 2009.

U.S. Appl. No. 10/374,000, filed Feb. 25, 2003; Office Action mailed Sep. 30, 2008.

U.S. Appl. No. 11/320,223, filed Dec. 28, 2005 Final Office Action dated Jun. 19,2009.

U.S. Appl. No. 11/320,223, filed Dec. 28, 2005 Non-Final Office Action dated Jan. 21, 2010.

U.S. Appl. No. 11/380,124, filed Apr. 25, 2006 Final Office Action dated Sep. 21, 2009.

U.S. Appl. No. 11/380,124, filed Apr. 25, 2006 Non-Final Office Action dated Apr. 26, 2010.

U.S. Appl. No. 11/380,621, filed Apr. 27, 2006 Final Office Action dated Jan. 14, 2010.

U.S. Appl. No. 11/380,621, filed Apr. 27, 2006 Final Office Action dated Jan. 23, 2009.

U.S. Appl. No. 11/380,621, filed Apr. 27, 2006 Non-Final Office Action dated Jul. 1, 2009.

U.S. Appl. No. 11/380,621, filed Apr. 27, 2006 Non-Final Office Action dated Jun. 6, 2008.

U.S. Appl. No. 11/725,287, filed Mar. 19, 2007; Non-final Office Action issued on Dec. 3, 2008.

U.S. Appl. No. 11/725,287, filed Mar. 19, 2007; Non-final Office Action issued on Jun. 12, 2009.

U.S. Appl. No. 11/725,287, filed Mar. 19, 2007; Non-final Office Action issued on Mar. 29, 2010.

U.S. Appl. No. 12/023,280, filed Jan. 31, 2008 Final Office Action dated Mar. 9, 2010.

U.S. Appl. No. 12/023,280, filed Jan. 31, 2008 Non-Final Office Action dated Jul. 23, 2009.

U.S. Appl. No. 12/023,280, filed Jan. 31, 2008 Non-Final Office Action dated Oct. 5, 2009.

U.S. Appl. No. 12/143,377, filed Jun. 20, 2008, Non-final Office Action mailed Apr. 27, 2009.

U.S. Appl. No. 12/143,377, filed Jun. 20, 2008; Final Office Action mailed Oct. 19, 2009.

U.S. Appl. No. 12/175,182, filed Jul. 17,2008; Non-final Office Action mailed Sep. 3, 2009.

U.S. Appl. No. 12/419,957, filed Apr. 7, 2009 Non-Final Office Action dated Feb. 18, 2010.

U.S. Appl. No. 12/419,957, filed Apr. 7, 2009 Non-Final Office Action dated Jun. 30, 2009.

U.S. Appl. No. 12/420,007, filed Apr. 7, 2009 Final Office Action dated Feb. 18, 2010.

U.S. Appl. No. 12/420,007, filed Apr. 7, 2009 Non-Final Office Action dated Jul. 14, 2009.

U.S. Appl. No. 29/239,163, filed Sep. 27, 2005.

U.S. Appl. No. 29/247,954, filed Jul. 21, 2006 Non-Final Office Action dated Apr. 6, 2007.

U.S. Appl. No. 29/247,954, filed Jul. 21, 2006 Notice of Allowability dated Jul. 30, 2007.

U.S. Appl. No. 29/247,954, filed Jul. 21, 2006.

U.S. Appl. No. 60/658,518, filed Mar. 4, 2005, publicly accessible Oct. 5, 2006.

Vergara, et al., "Adverse Reactions to Contrast Medica in CT: Effects of Temperature and Ionic Property." Radiology, vol. 199, No. 2, May 1996.

Vogelzang, Robert L., "Power Injection Through Central Venous Catheters: Physiological and Hemodynamic Considerations." The McGaw Medical Center of Northwestern University, Feinberg School of Medicine.

Wells, S. "Venous Access in Oncology and Haematology Patients: Part One." Nursing Standard, vol. 22, No. 52, pp. 39-46, Sep. 3, 2008.

Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.

U.S. Appl. No. 10/374,000, filed Feb. 25, 2003 Advisory Action dated Jan. 23, 2007.

U.S. Appl. No. 10/374,000, filed Feb. 25, 2003 ; Non-final Office Action mailed Mar. 20, 2008.

U.S. Food and Drug Administration, "Guidance for Institutional Review Boards and Clinical Investigators 1998 Update: Medical Devices." Version Sep. 10, 2008.

Sullivan et al. "Radiopaque Markers on Mammary Implants." American Journal of Roentgenology 153(2):428, Aug. 1989.

Steinbach, Barbara G. , Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993.

Soloman, et al., "CIN Strategies: Anticipate, Manage, Prevent." Supplement to Imaging Economics, May 2007.

Smith, Lisa Hartkoph, "Implanted Ports, Computed Tomography, Power Injectors, and Catheter Rupture." Clinical Journal of Oncology Nursing, vol. 12 , No. 5. Oct. 2008.

Sanelli, et al., "Safety and Feasibility of Using a Central Venous Catheter for Rapid Contrast Injection Rates." American Journal of Radiology, vol. 183, pp. 1829-1834, Dec. 2004.

Sandstede, Joern, "Pediatric CT," available online at www.multislice-ct.com, MultiSLICE-CT.com, version 02, May 2, 2003.

Port-A-Cath P.A.S. PORT Systems by Deltec, Product Specifications, 1999.

LAP-BAND System Access Port Fill Guide I, "9.75/10.0 cm LAP-BAND System vs. 11 cm LAP-BAND System: For Product Manufactured Prior to Jul. 2001" BioEnterics Corporation.

Johnson, Kathleen A., "Power Injectable Portal Systems." Journal of Radiology Nursing, vol. 28, Issue 1, Mar. 2009.

International Application No. PCT/US2009/062854 filed Oct. 30, 2009 Written Opinion dated Dec. 10, 2009.

International Application No. PCT/US2009/062854 filed Oct. 30, 2009 International Search Report dated Dec. 10, 2009.

"Extravasation of Radiologic Contrast." PA-PSRS Patient Safety Advisory—vol. 1, No. 3, Sep. 2004.

Biffi, R. et al. "Use of totally implantable central venous access ports for high-dose chemotherapy and peripheral blood stem cell transplantation: results of a monocentre series of 376 patients." Annals of Oncology 15:296-300, 2004.

Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.

Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001.

Costa, Nancy, "More Than Skin Deep: An Overview of Iodinated Contrast Media.." Journal for the Association for Vascular Access, vol. 8, No. 4, 2003.

Costa, Nancy, "Understanding Contrast Media." Journal of Infusion Nursing, vol. 27, No. 5, Sep./Oct. 2004.

Extreme Accessä Bard Access Systems, Inc. Product Brochure, 2003.

Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.

Hou, Shaw-Min et al. "Comparisons of Outcomes and Survivals for Two Central Venous Access Port Systems." Journal of Surgical Oncology, 91:61-66, 2005.

International Application No. PCT/US1999/028695 filed Dec. 3, 1999 International Preliminary Examination Report dated Apr. 21, 2001.

International Application No. PCT/US1999/028695 filed Dec. 3, 1999 International Search Report dated Apr. 11, 2000.

International Application No. PCT/US2006/008022 filed Mar. 6, 2006 International Preliminary Report on Patentability dated Dec. 9, 2007.

International Application No. PCT/US2006/008022 filed Mar. 6, 2006 Written Opinion dated Apr. 9, 2007.

International Application No. PCT/US2006/015695 filed Apr. 25, 2006 International Search Report dated Jan. 11, 2007.

International Application No. PCT/US2006/015695 filed Apr. 25, 2006 Written Opinion dated Oct. 27, 2007.

International Application No. PCT/US2006/016056 filed Apr. 27, 2006 International Preliminary Report on Patentability dated Oct. 30, 2007.

International Application No. PCT/US2006/016056 filed Apr. 27, 2006 International Search Report dated Sep. 20, 2006.

International Application No. PCT/US2006/016056 filed Apr. 27, 2006 Written Opinion dated Oct. 27, 2007.

International Application No. PCT/US2006/049007 filed Dec. 21, 2006 International Preliminary Report on Patentability dated Jul. 1, 2008.

International Application No. PCT/US2007/006776 (PCT Written opinion, dated Dec. 18, 2007).

International Application No. PCT/US2007/006776 International Preliminary Report on Patentability dated Jan. 2, 2009.

International Application No. PCT/US2007/006776 International Search Report, dated Dec. 18, 2007.

International Application No. PCT/US2007/011015 (International Preliminary Report on Patentability dated Oct. 29, 2008).

International Application No. PCT/US2007/011015 (PCT Search Report dated Jun. 10, 2008).

International Application No. PCT/US2007/011015 (PCT Written Opinion dated Jun. 10, 2008).

International Application No. PCT/US2007/011456 (PCT Search Report dated Aug. 28,2008).

International Application No. PCT/US2007/011456 (PCT Written Opinion dated Aug. 28, 2008).

International Application No. PCT/US2008/010520 (PCT Search Report dated Feb. 24, 2009).

International Application No. PCT/US2008/010520 (PCT Written Opinion dated Feb. 24, 2009).

International Application No. PCT/US2008/067679; PCT Search Report mailed on Sep. 30, 2008.

International Application No. PCT/US2008/067679; PCT Written Opinion mailed on Sep. 30, 2008.

International Application No. PCT/US2008/070330 filed Jul. 17, 2008; PCT Search Report.

International Application No. PCT/US2008/070330 filed Jul. 17, 2008; PCT Written Opinion.

International Application No. PCT/US2008/070345; PCT Search Report mailed on Dec. 1, 2008.

International Application No. PCT/US2008/070345; PCTWritten Opinion mailed on Dec. 1, 2008.

International Application No. PCT/US2008/078976 (PCT Search Report and Written Opinion dated Apr. 3, 2009).

U.S. Appl. No. 29/284,454, filed Sep. 7, 2007, titled Implantable Port Device, listing John A. Zawacki and Annemarie Boswell as inventors, in which a Continued Prosecution Application was filed on Jan. 30, 2008.

U.S. Appl. No. 29/284,456, filed Sep. 7, 2007, titled Implantable Port Device, listing John A. Zawacki and Annemarie Boswell as inventors.

Office Action issued on Feb. 13, 2006, in U.S. Appl. No. 10/374,000 (published as U.S. Publication No. 2003/0181878 A1).

Response to Office Action dated May 12, 2006, filed in U.S. Appl. No. 10/374,000 (published as U.S. Publication No. 2003/0181878 A1) in which a Continued Prosecution Application was filed on Jan. 30, 2008.

Office Action issued on Jul. 28, 2006, in U.S. Appl. No. 10/374,000 (published as U.S. Publication No. 2003/0181878 A1).

Response to Office Action dated Nov. 28, 2006, filed in U.S. Appl. No. 10/374,000 (published as U.S. Publication No. 2003/0181878 A1).

Office Action issued on Feb. 28, 2007, in U.S. Appl. No. 10/374,000 (published as U.S. Publication No. 2003/0181878 A1).

Response to Office Action dated May 28, 2007, filed in U.S. Appl. No. 10/374,000 (published as U.S. Publication No. 2003/0181878 A1).

Office Action issued on Aug. 28, 2007, in U.S. Appl. No. 10/374,000 (published as U.S. Publication No. 2003/0181878 A1).

Response to Office Action dated Oct. 31, 2007, filed in U.S. Appl. No. 10/374,000 (published as U.S. Publication No. 2003/0181878 A1 ).

* cited by examiner

ACCESS PORT IDENTIFICATION SYSTEMS AND METHODS

CROSS-REFERENCE TO RELATED APPLICATION

This claims the benefit of U.S. patent application Ser. No. 60/658,518, filed 4 Mar. 2005, the disclosure of which is incorporated, in its entirety, by this reference.

BACKGROUND

Access ports provide a convenient method to repeatedly deliver a substance to remote areas of the body without utilizing surgical procedures. Ports are totally implantable within the body (i.e. subcutaneously) and may permit the infusion of medicine, parenteral solutions, blood products, or other fluids. Additionally, ports may also be used for blood sampling.

A typical port typically includes a housing assembly, a septum, and an outlet. The housing assembly and septum define a reservoir which is accessible through the septum. The outlet of the housing may communicate with a catheter which accesses a vein. Thus, the catheter may be employed for delivering a fluid from the port to a remote location in the body, for example, the superior vena cava.

In common practice, a port is implanted within the body and the catheter is routed to a remote area where a fluid is desired to be delivered. To deliver the fluid, a caregiver locates the septum of the port by palpation of a patient's skin. Port access is accomplished by percutaneously inserting a needle, typically a non-coring needle, through the septum of the port and into the reservoir. A fluid, such as a drug or other beneficial substance, may then be administered by bolus injection or continuous infusion into the reservoir. Thus, the fluid may flow through the reservoir into the catheter and finally to the site were the fluid is desired.

Ports generally come in two different types, surgical and cosmetic. Surgical ports may typically be used for delivering medicinal substances, including chemotherapy drugs which may be harmful to surrounding tissue, or for sampling blood. Cosmetic ports, on the other hand, are utilized to deliver saline or some other non-reactive substance to a prosthesis which supplements a body feature.

Generally, conventional access ports of different manufacturers or models may typically exhibit substantially similar geometries that may not be differentiable with respect to one another. Accordingly, once an access port is implanted, it may be difficult to determine the model, style, or design of the access port. Such uncertainty may be undesirable, at least for replacement timing purposes, among other reasons, especially if identification of the implanted access port is difficult to otherwise determine.

Thus, it would be advantageous to provide an access port which provides at least one identifiable characteristic that may be sensed or otherwise determined subsequent to subcutaneous implantation of the access port.

SUMMARY

One aspect contemplated by the instant disclosure relates to an access port for providing subcutaneous access to a patient. Such an access port may comprise a body for capturing a septum for repeatedly inserting a needle therethrough into a cavity defined within the body. Further, an access port according to the instant disclosure may include at least one feature structured and configured for identification of the access port subsequent to subcutaneous implantation.

Another aspect contemplated by the instant disclosure relates to a method of identifying a subcutaneously implanted access port. More particularly, a subcutaneously implanted access port may be provided and at least one feature of the subcutaneously implanted access port may be perceived. Further, the subcutaneously implanted access port may be identified in response to perceiving the at least one feature.

A further aspect of the instant disclosure relates to an access port for providing subcutaneous access to a patient. Particularly, such an access port may comprise a body configured for capturing a septum for repeatedly inserting a needle therethrough into a cavity defined within the body. Further, the access port may comprise at least one feature structured to identify the access port as being power injectable subsequent to subcutaneous implantation.

Features from any of the above mentioned embodiments may be used in combination with one another in accordance with the instant disclosure. In addition, other features and advantages contemplated by the instant disclosure will become apparent to those of ordinary skill in the art through consideration of the ensuing description, the accompanying drawings, and the appended claims.

DETAILED DESCRIPTION

Figure 1A:
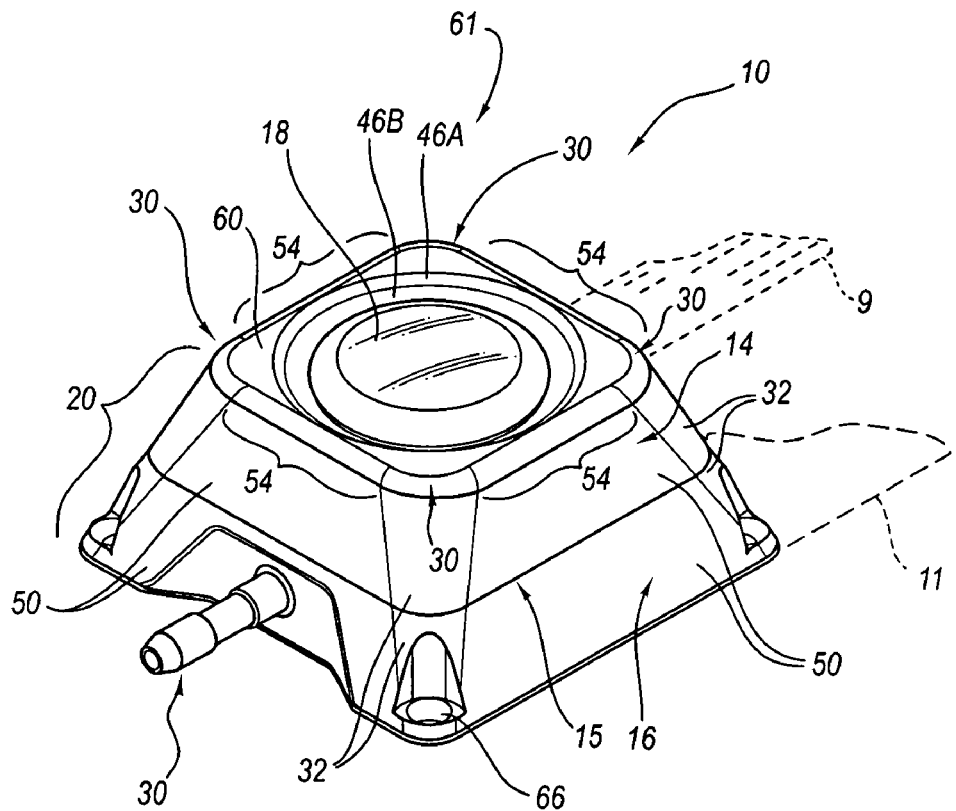
FIG. 1A shows a perspective view of an embodiment of an access port according to the instant disclosure.

The instant disclosure relates generally to percutaneous access and, more specifically, to methods and devices associated with percutaneous access. Generally, the instant disclosure relates to an access port for subcutaneous implantation. In one embodiment, an access port may allow a physician or other medical personnel to obtain long term percutaneous access to the interior of a patient's body. Employing an access port for percutaneous access may reduce the opportunity for infection by inhibiting fluid connections (that extend into the interior of a patient's body) from the patient's skin and from the external environment. The access device allows access to the interior of the patient without requiring a needle to pierce the skin. Further, internal components, such as a catheter or a valve, may be replaced without a surgical procedure. Features or aspects of the instant disclosure may apply to any such access ports for subcutaneous access to a patient, without limitation. The access port may be injected by hand (e.g., via a syringe including a needle) for example, or may be injected and pressurized by mechanical assistance (e.g., a so-called power injectable port).

Power injectable ports may be employed in, among other processes, for example, computed tomography ("CT") scanning processes. More particularly, a so-called "power injector" system may be employed for injecting contrast media into a peripherally inserted intravenous (IV) line. For example, such power injectors or injection systems may be commercially available from Medrad, Inc., a subsidiary of Schering AG, Germany and may be marketed under the trademark STELLANT®. Because fluid infusion procedures are often defined in terms of a desired flow rate of contrast media, such power injection systems are, in general, controllable by selecting a desired flow rate.

More specifically, the instant disclosure relates to an access port having at least one perceivable or identifiable feature for identifying the access port, wherein the identifiable feature is perceivable after the access port is implanted within a patient. For example, at least one or perhaps multiple identifiable feature(s) of an access port contemplated by the instant disclosure may be correlative to information (e.g., a manufacturer's model or design) pertaining to the access port. Thus, an identifiable feature from an access port of a particular model may be unique in relation to most if not all other identifiable features of another access port of a different models or design. Of course, the at least one identifiable feature of an access port contemplated by the instant disclosure may be further correlative with any information of interest, such as type of port, catheter type, date of manufacture, material lots, part numbers, etc. In one example, at least one identifiable feature of an access port may be correlative with the access port being power injectable. In this way, once at least one identifiable feature of an access port is observed or otherwise determined, correlation of such at least one feature of an access port may be accomplished, and information pertaining to the access port may be obtained.

In one embodiment, at least one feature may be perceived by palpation (i.e., to examine by touch), by way of other physical interaction, or by visual observation. Accordingly, a person of interest may touch or feel the access port through the skin to perceive at least one identifying characteristic thereof. In another embodiment, at least one identifiable feature may be perceived via x-ray or ultrasound imaging. In yet a further embodiment, at least one identifiable feature may be perceived through magnetic, light, or radio energy interaction or communication with the access port.

Figure 1B:
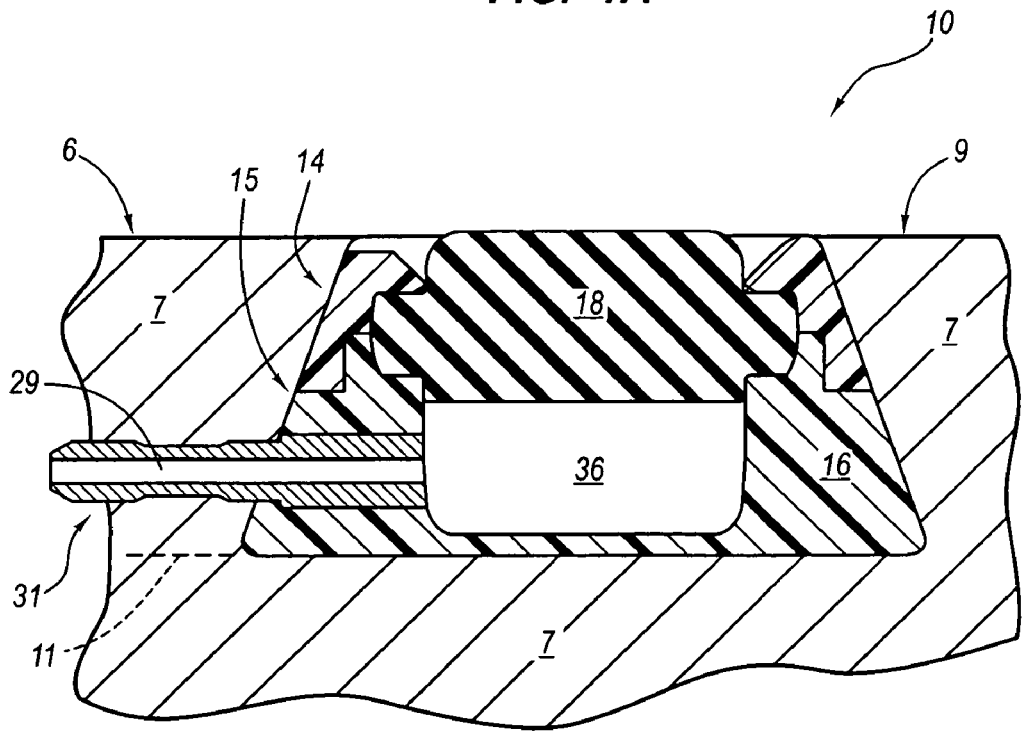
FIG. 1B shows a schematic side cross-sectional view the access port shown in FIG. 1A.

Turning to the embodiment wherein at least one feature may be perceived through palpation, other physical interaction, or visual observation, a topography or exterior surface feature of an access port contemplated by the instant disclosure may be configured for perception. For example, referring to FIGS. 1A and 1B, an exemplary access port 10 contemplated by the instant disclosure is shown. FIGS. 1A and 1B show a perspective view and a schematic side cross-sectional view, respectively, of an access port 10 for allowing percutaneous or otherwise internal access to a patient's body. Access port 10 includes a housing or body 20 defined by a cap 14 and a base 16. Cap 14 and base 16, as known in the art, may be configured for capturing therebetween a septum 18. As shown in FIG. 1A, cap 14 and base 16 may matingly engage one another along a mating line 15. Cap 14 and base 16 may be secured or affixed to one another via mechanical fasteners such as screws or other fastening devices, may be adhesively affixed to one another, or may be affixed to one another as known in the art. Further, cap 14, base 16, and septum 18 may collectively define a cavity 36 in fluid communication with a lumen 29 of outlet stem 31.

The body 20 may be implanted in a patient 7, as shown in FIG. 1B, to dispose the cavity 36 subcutaneously within the patient 7. Also, suture apertures 66 (FIG. 1A) may be used to affix the access port 10 within the patient 7, if desired. After the body 20 is implanted in a patient 7, the upper surface of the septum 18 may be substantially flush with the surface of the skin 6 of the patient 7 and may be repeatedly punctured for creating a percutaneous passageway from the exterior of the skin of the patient into the cavity 36. The outlet stem 31 may create a fluid-communicative passageway from the cavity 36 through the outlet stem 31 and into the interior of the patient 7. A catheter may be coupled to the outlet stem 31 for fluid communication with the cavity 36 and for transferring fluid from the cavity 36 to a desired remote location from the cavity 36 and within a patient 7.

Body 20 of access port 10 may comprise a bio-compatible material such as polysulfone, titanium, or any other suitably bio-compatible material as known in the art. Accordingly, the body 20 may be formed from a bio-compatible plastic material. If desired, the body 20 may comprise a penetrable material for penetration by sutures or needles. In another embodiment, and as discussed further hereinbelow, body 20 may comprise an impenetrable material such as, for instance, a metal if desired. Body 20 may include a concave bottom or, in another embodiment, may include a flat bottom, without limitation.

According to the instant disclosure, access port 10 may comprise a body 20 exhibiting at least one identifiable feature. More particularly, as shown in FIG. 1A, body 20 may exhibit a partial generally pyramidal shape (i.e., a polygonal base having surfaces for each side of the polygon extending toward a common vertex otherwise known as a frustum). Generally, a body 20 of an access port 10 may exhibit a partial pyramidal shape extending between a generally quadrilateral shaped base positioned at reference plane 11 and a generally quadrilateral shaped upper base positioned at reference plane 9. Reference planes 9 and 11 will not be shown in FIGS. 2-21, for clarity; however, reference to planes 9 or 11 with respect to FIGS. 2-21, as used herein, will refer to corresponding reference planes analogous to reference planes 9 and 11 as shown in FIGS. 1A and 1B.

As shown in FIG. 1A, the exterior of access port 10 is substantially defined by four substantially planar side surfaces 50 connected to one another by radiuses 32. In addition, the upper topography 61 of access port 10 is defined by upper surface 60 in combination with chamfers 46A and 46B and may be further defined by the upper surface of septum 18. Explaining further, the outer periphery of upper topography 61 may be described as a generally quadrilateral exterior formed by side regions 54 and having rounded corner regions 30 adjacent side regions 54. Such a configuration may provide an access port having at least one feature that may be perceived by palpation.

It may be appreciated that there are many variations to the geometry of access port 10 as shown in FIG. 1A. For instance, while the body 20 of access port 10 may be described as a partially pyramidal shape or frustum, the instant disclosure is not so limited. Rather, one or more of side surfaces 50 may be oriented at as may be desired, without reference to any other side surfaces 50. Accordingly, for example, one of surfaces 50 may be substantially vertical while the remaining surfaces 50 may be oriented at respective, selected angles. Furthermore, it should be understood that FIG. 1A is merely exemplary and that the dimensions and shape as shown in FIG. 1A may vary substantially while still being encompassed by the instant disclosure.

Figure 2:
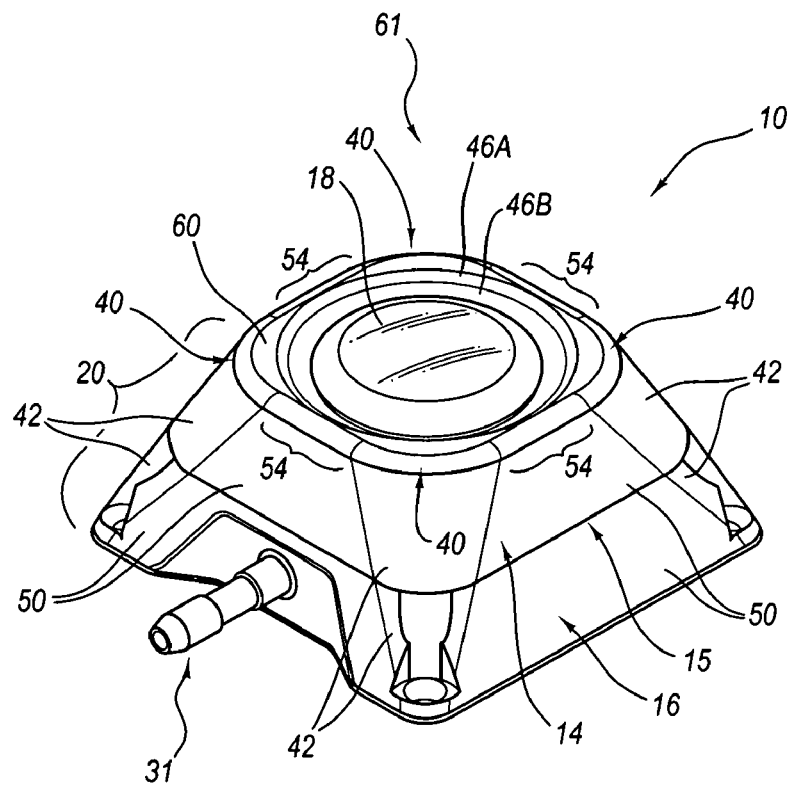
FIG. 2 shows a perspective view of an embodiment of an access port according to the instant disclosure.

FIG. 2 shows a perspective view of another embodiment of access port 10 according to the instant disclosure. As shown in FIG. 2, the exterior of access port 10 is substantially defined by a generally parallelogram-shaped base (positioned at reference plane 11 as shown in FIGS. 1A and 1B) extending generally pyramidally to a generally parallelogram-shaped upper surface (positioned at reference plane 9 as shown in FIGS. 1A and 1B). As shown in FIG. 2, radiuses 42 may be larger than radiuses 32 as shown in FIG. 1A. Furthermore, the upper topography 61 of access port 10 as shown in FIG. 2 may include rounded corner regions 40 which are larger than rounded corner regions 30 as shown in FIG. 1A. Thus, FIG. 2 shows an exemplary embodiment of an access port 10 that may be perceivably distinguishable from access port 10 as shown in FIGS. 1A and 1B. For example, a difference between one exterior of an access port contemplated by the instant disclosure and another exterior of a different access port contemplated by the instant disclosure may be determined by way of palpation.

In another embodiment, in another aspect contemplated by the instant disclosure, a template may be employed for perceiving at least one feature of an access port. For instance, a complementarily-shaped template may be positioned over and abutted against an access port contemplated by the instant disclosure so as to determine if the access port matches or substantially corresponds to the shape of the template. Such a process may reliably indicate or perceive at least one feature of an access port contemplated by the instant disclosure. Of course, a plurality of templates corresponding to different models of access ports may be serially engaged with an unknown access port so as to perceive at least one feature thereof. Such a process may allow for identification (e.g., of a model or manufacturer) of an access port contemplated by the instant disclosure.

Figure 3:
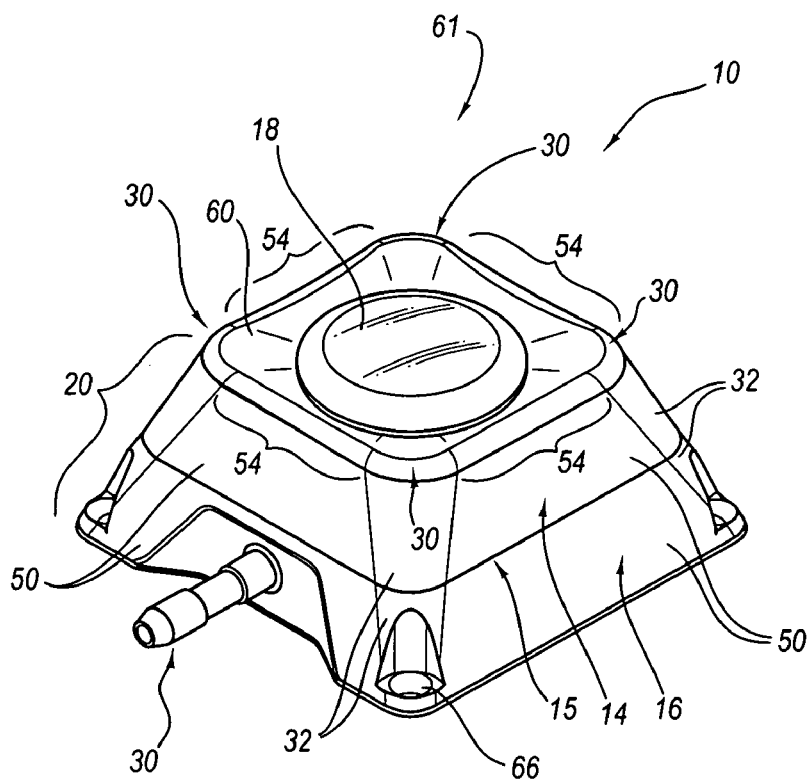
FIG. 3 shows a perspective view of an access port according to the instant disclosure.

In another aspect contemplated by the instant disclosure, an upper topography of an access port may include at least one feature for identifying the access port. For example, as shown in FIG. 3, upper surface 60 of access port 10 may be nonplanar. More specifically, upper surface 60 may be tapered or may arcuately extend downwardly (i.e., toward reference plane 11 as shown in FIGS. 1A and 1B) as it extends radially inwardly toward septum 18. Otherwise, access port 10, as shown in FIG. 3, may be configured substantially as described hereinabove with reference to FIGS. 1A and 1B. Thus, upper surface 60 is one exemplary example of at least one perceivable feature for identification of an access port contemplated by the instant disclosure.

Figure 4:
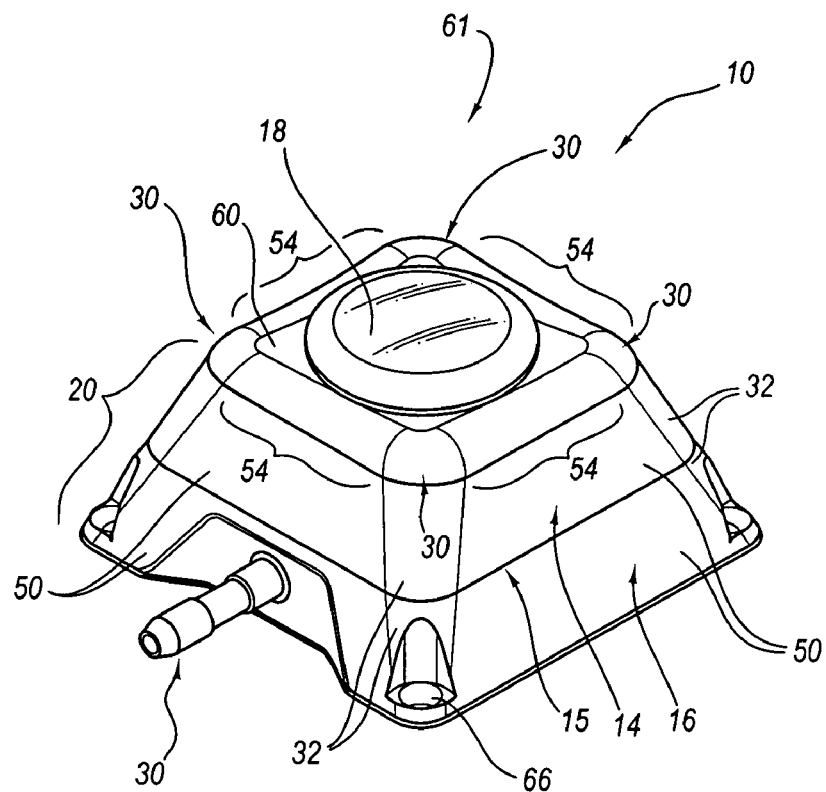
FIG. 4 shows a perspective view of an access port according to the instant disclosure.

In yet a further embodiment of an access port contemplated by the instant disclosure, side regions 54 extending between rounded corner regions 30 may exhibit at least one perceivable feature. For example, as shown in FIG. 4, access port 10 may include one or more side regions 54 that extend arcuately between adjacent rounded corner regions 30. Otherwise, access port 10, as shown in FIG. 4, may be configured substantially as described hereinabove with reference to FIGS. 1A and 1B. Side regions 54 may be congruent or symmetric with respect to one another or, in another embodiment, may be configured differently with respect to one another, without limitation.

Figure 5:
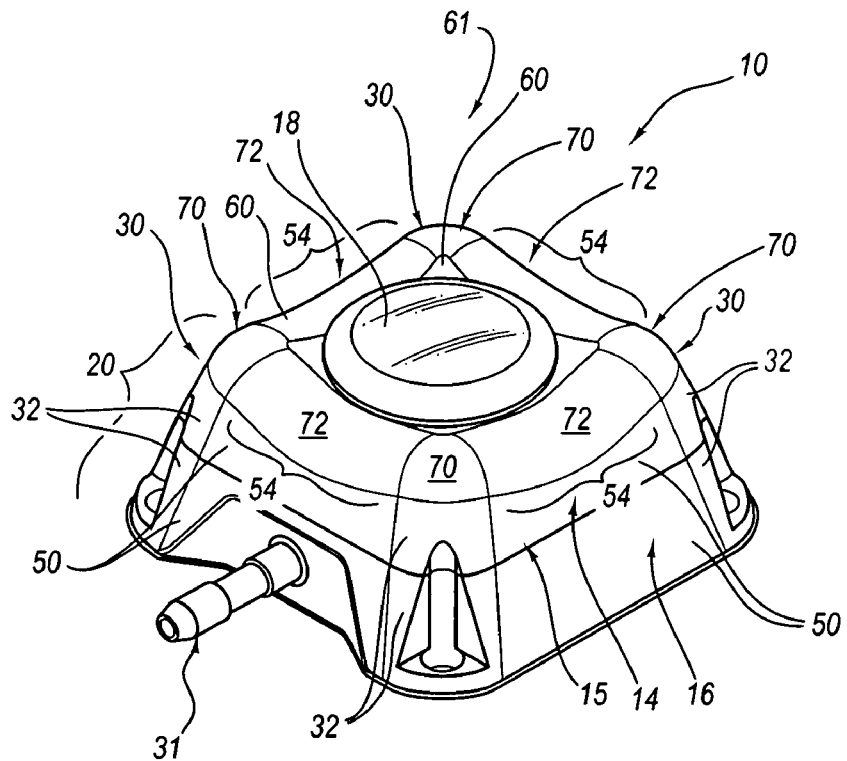
FIG. 5 shows a perspective view of an access port according to the instant disclosure.

FIG. 5 shows a further exemplary embodiment of an access port contemplated by the instant disclosure. More specifically, access port 10, as shown in FIG. 5, includes side regions 54 that form recessed regions 72 between adjacent rounded corner regions 30. Put another way, the upper topography 61 may include alternating recessed regions 72 and protruding regions 70 positioned generally about a periphery of septum 18. Otherwise, access port 10, as shown in FIG. 5, may be configured substantially as described hereinabove with reference to FIGS. 1A and 1B. Such a configuration may provide an access port having at least one identifiable feature.

Figure 6A:
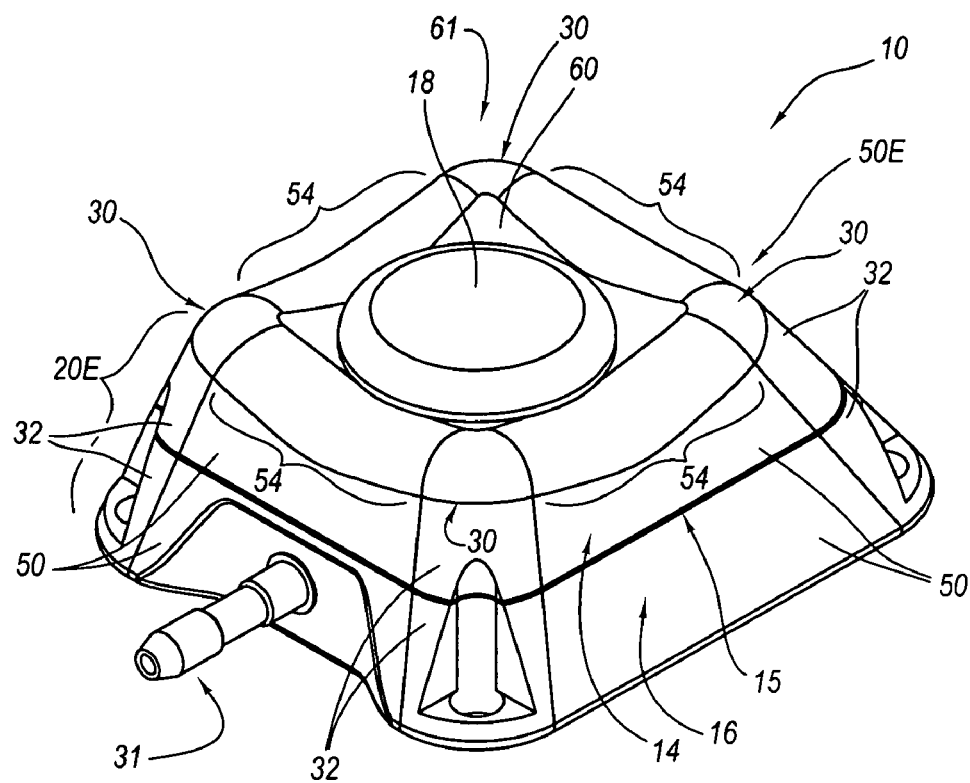
FIG. 6A shows a perspective view of an access port according to the instant disclosure.
Figure 6B:
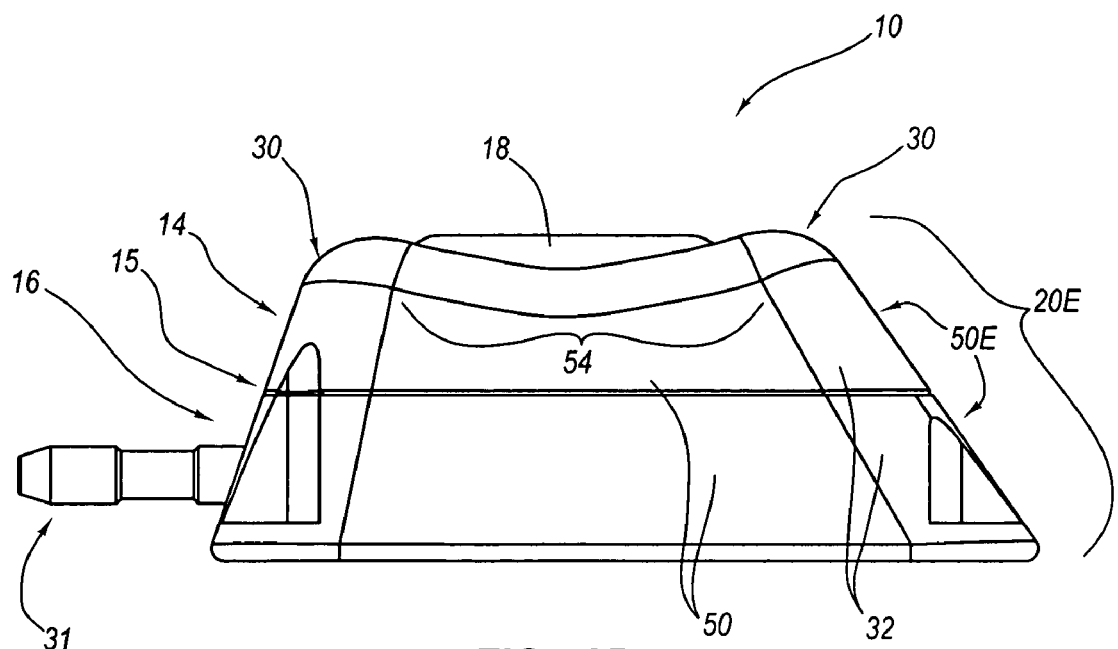
FIG. 6B shows a side view of the access port shown in FIG. 6A.

In a further embodiment of an access port contemplated by the instant disclosure, FIGS. 6A and 6B show a perspective view and a side view, respectively, of an access port 10 generally configured as is described with reference to FIG. 5 but having an elongated body 20E. More specifically, elongated body 20E of access port 10, as shown in FIGS. 6A and 6B, includes a side surface 50E that extends generally from upper topography 61 downwardly (i.e., toward reference plane 11 as shown in FIGS. 1A and 1B) and having a slope (e.g., an angle with respect to a vertical axis normal to an upper surface of septum 18) which is different from the other side surfaces 50. Otherwise, access port 10, as shown in FIG. 6, may be configured substantially as described hereinabove with reference to FIGS. 1A and 1B. Such a configuration may provide an elongated body 20E of an access port 10 having an elongated side portion.

Of course, one or more side surfaces of an access port according to the instant disclosure may be configured for forming a body exhibiting a selected shape as may be desired. An elongated body portion of an access port contemplated by the instant disclosure may form, in combination with other features as described hereinabove or, in another embodiment, taken alone, at least one perceivable feature for identification of an access port according to the instant disclosure.

Figure 7:
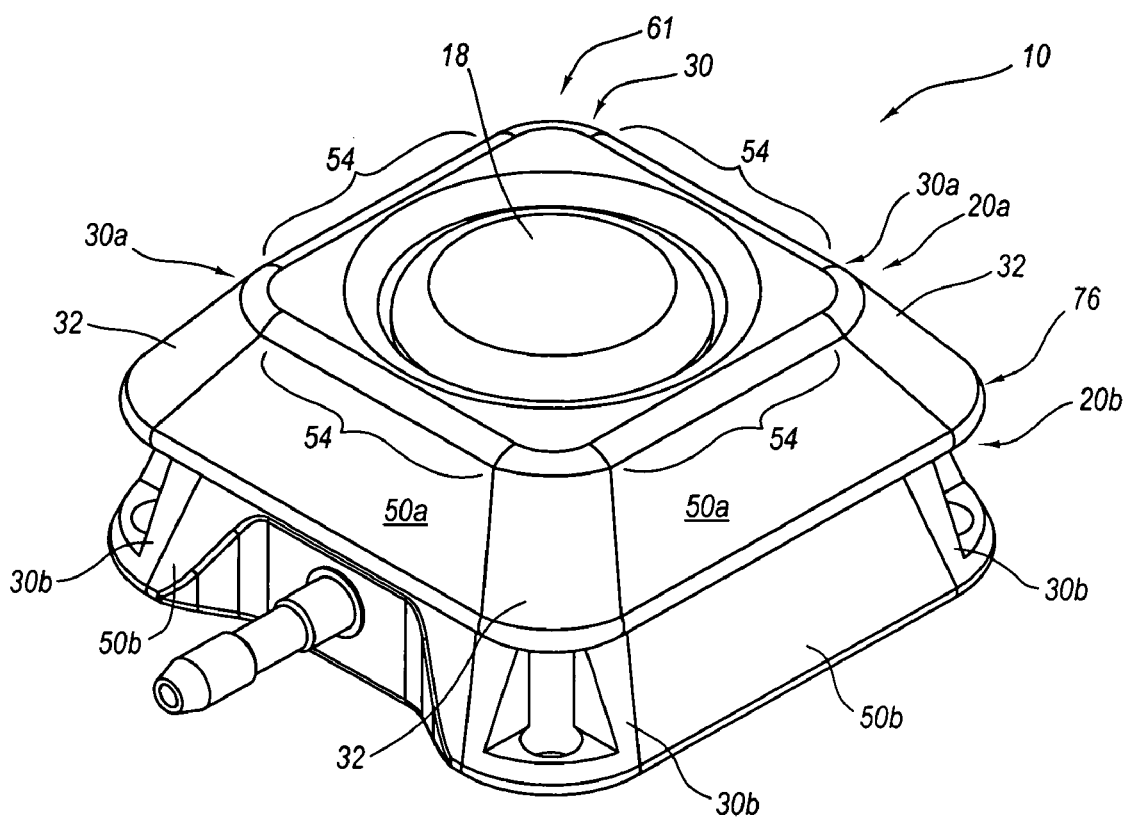
FIG. 7 shows a perspective view of an access port according to the instant disclosure.

FIG. 7 shows a further embodiment of an access port encompassed by the instant disclosure. Particularly, as shown in FIG. 7, access port 10 may include an upper body portion 20a and a lower body portion 20b. Furthermore, each of upper body portion 20a and lower body portion 20b may exhibit a partial pyramidal shape (i.e., a frustum), wherein the body portions 20a and 20b are stacked vertically with respect to one another. Accordingly, upper body portion 20a may form an overhanging rim feature 76 extending along a periphery of access port 10. Explaining further, lower body portion 20b may have an exterior substantially defined by side surfaces 50b and rounded corner regions 30b, while upper body portion 20a may have an exterior substantially defined by side surfaces 50a, rounded corner regions 30a, and upper topography 61. It may be appreciated that overhanging rim feature 76 may be sized and configured for perception via palpation. Such a configuration may provide a suitable access port for delivery of a beneficial or medicinal substance, the access port being identifiable (e.g., by model number, manufacturer, etc.) after implantation.

Figure 8:
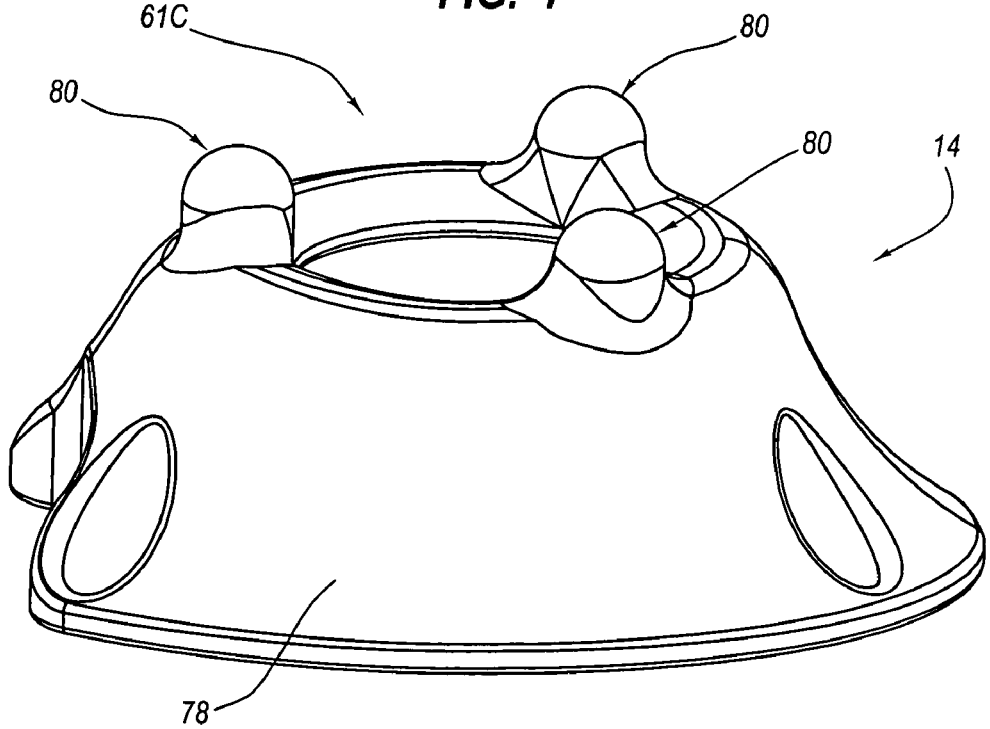
FIG. 8 shows a simplified perspective view of a cap for forming an access port according to the instant disclosure.

It should be understood that the instant disclosure contemplates access ports having an exterior geometry that is not quadrilateral in nature. Rather, the instant disclosure contemplates that an access port may have an exterior which is generally cylindrical, generally conical, generally elliptical, generally oval, or an exterior that is otherwise arcuate in nature. Specifically, the instant disclosure contemplates that an access port having a substantially rounded or arcuate exterior may include at least one feature configured for identification of the access port after implantation. For example, as shown in FIG. 8, shows a cap 14 that exhibits an exterior surface 78 that is substantially conical. Cap 14 may be assembled to a suitable base (not shown) for capturing a septum (not shown) as described hereinabove to form an access port 10 as generally described with reference to FIGS. 1-7.

The instant disclosure further contemplates that at least one protrusion, protruding region, recess, recessed region, undulation, or adjacent features of different elevation may comprise a feature for identifying an access port contemplated by the instant disclosure. More specifically, upper topography 61C, as shown in FIG. 8, may include a plurality of protrusions 80. Protrusions 80 may exhibit partially spherical upper surfaces that transition into a lower portion of cap 14. In further detail, protrusions 80 may be circumferentially spaced about the periphery of septum (not shown) as may be desired. In one embodiment, a plurality of protrusions 80 may be symmetrically circumferentially spaced about the periphery of septum (not shown). More generally, at least one protrusion 80 may be sized, configured, and positioned for forming at least one identifiable feature of an access port. Of course, at least one protrusion 80 may be structured for facilitating comfort of a patient within which the access port is implanted. As may be appreciated, at least one protrusion 80 or more than one protrusion 80 may be included in an upper topography 61C of an access port (not shown) contemplated by the instant disclosure.

Figure 9:
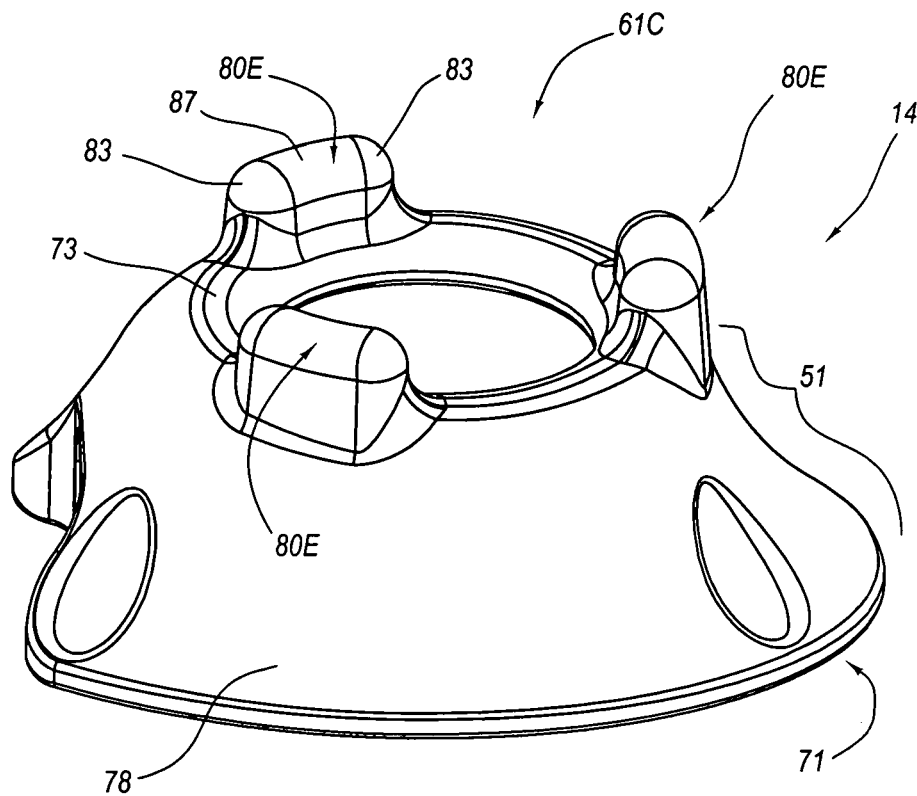
FIG. 9 shows a simplified perspective view of a cap for forming an access port according to the instant disclosure.

FIG. 9 shows another embodiment of a cap 14 including at least one protrusion 80E for forming and identifying an access port contemplated by the instant disclosure after implantation thereof within a patient. Protrusions 80E may extend circumferentially about a center of revolution. Thus, protrusions 80E may exhibit a body 87 portion circumferentially extending between rounded ends 83. Further, cap 14 may have an exterior surface 78 that is substantially symmetric about an axis of revolution. More generally, body 20 may extend from a generally circular, generally elliptical, or generally oval base positioned at a lower extent 71 of the cap 14 to an upper generally circular, generally elliptical, or generally oval cross section that is smaller than a cross section of the base and is positioned at an upper extent 73 (without considering protrusions 80E) of the cap 14. In addition, side surface 51, as shown in FIG. 9, extends arcuately between the base and the upper topography 61 of cap 14. Side surface 51 may extend in a generally tapered or conical fashion, may exhibit a radius or other arcuate shape, or may otherwise transition between a cross section of the base of the access port to a cross section proximate the upper topography 61C thereof.

Figure 10:
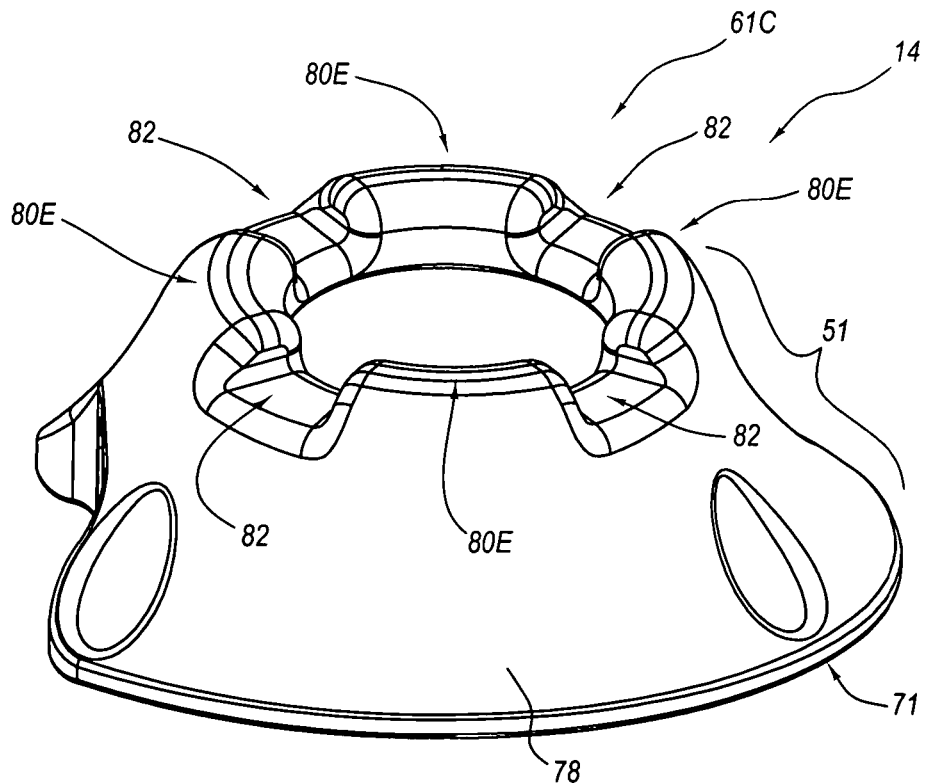
FIG. 10 shows a simplified perspective view of a cap for forming an access port according to the instant disclosure.
Figure 11:
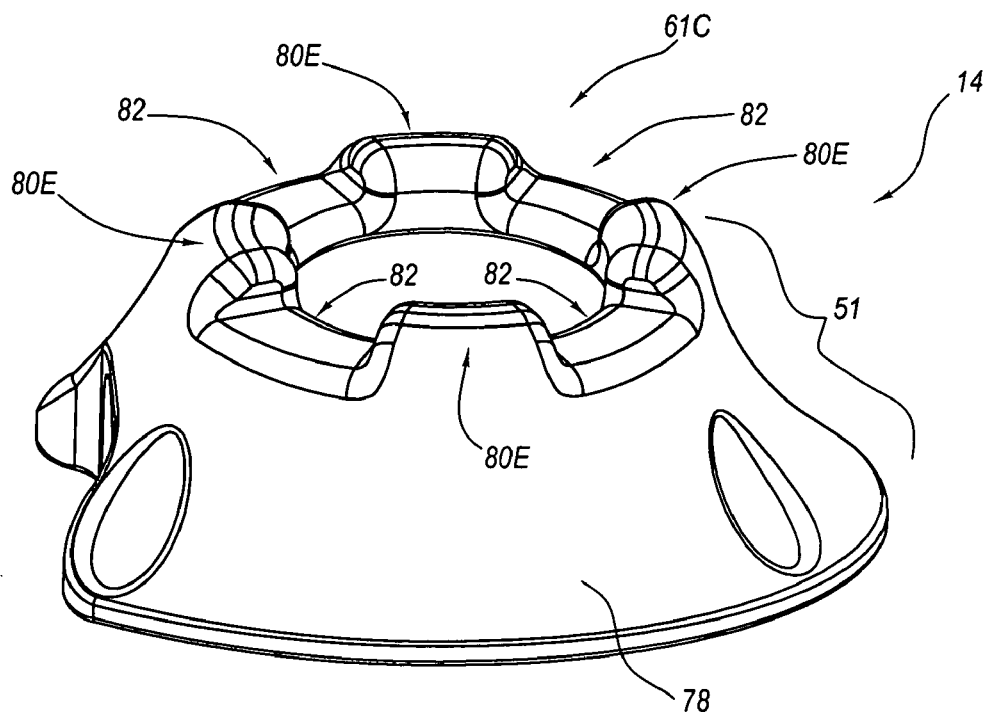
FIG. 11 shows a simplified perspective view of a cap for forming an access port according to the instant disclosure.
Figure 12:
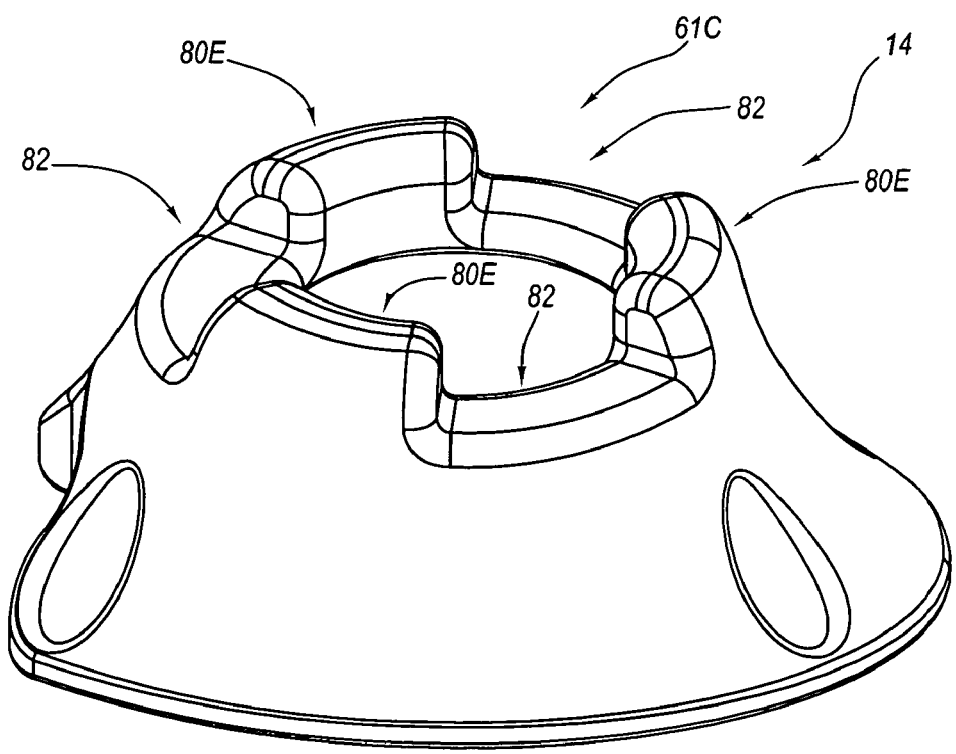
FIG. 12 shows a simplified perspective view of a cap for forming an access port according to the instant disclosure.

Further, FIG. 10 shows an embodiment of a cap 14 for forming an access port contemplated by the instant disclosure having an upper topography 61C thereof comprising alternating circumferentially extending protrusions 80E and circumferentially extending recesses 82, wherein the circumferentially extending protrusions 80E are circumferentially larger than the circumferentially extending recesses 80E. In another embodiment of an access port contemplated by the instant disclosure, FIG. 11 shows a perspective view of a cap 14 having an upper topography 61C thereof comprising alternating circumferentially extending protrusions 80E and circumferentially extending recesses 82, wherein the circumferentially extending protrusions 80E and the circumferentially extending recesses 82 are substantially equal in (circumferential) sized or extension. In yet a further embodiment of a cap 14 for forming an access port contemplated by the instant disclosure, FIG. 12 shows a perspective view of a cap 14 having an upper topography 61C thereof comprising three circumferentially extending protrusions 80E and three circumferentially extending recesses 82, arranged so as to alternate circumferentially, wherein the circumferentially extending protrusions 80E and the circumferentially extending recesses 82 are substantially equal in (circumferential) size.

Figure 13:
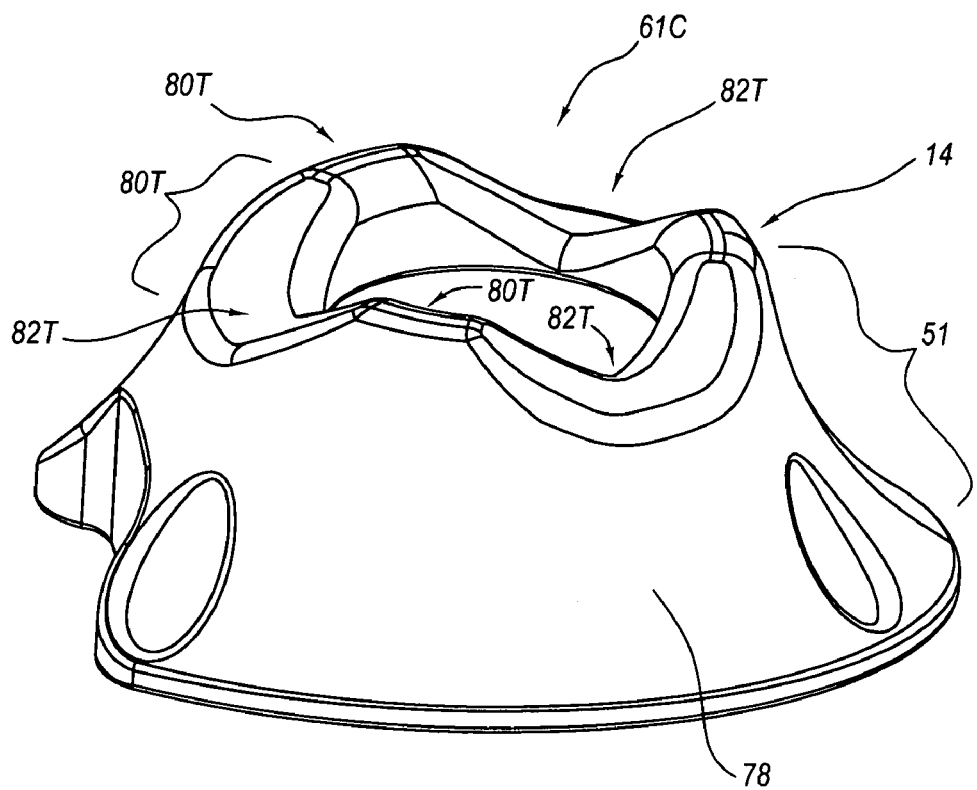
FIG. 13 shows a simplified perspective view of a cap for forming an access port according to the instant disclosure.
Figure 14:
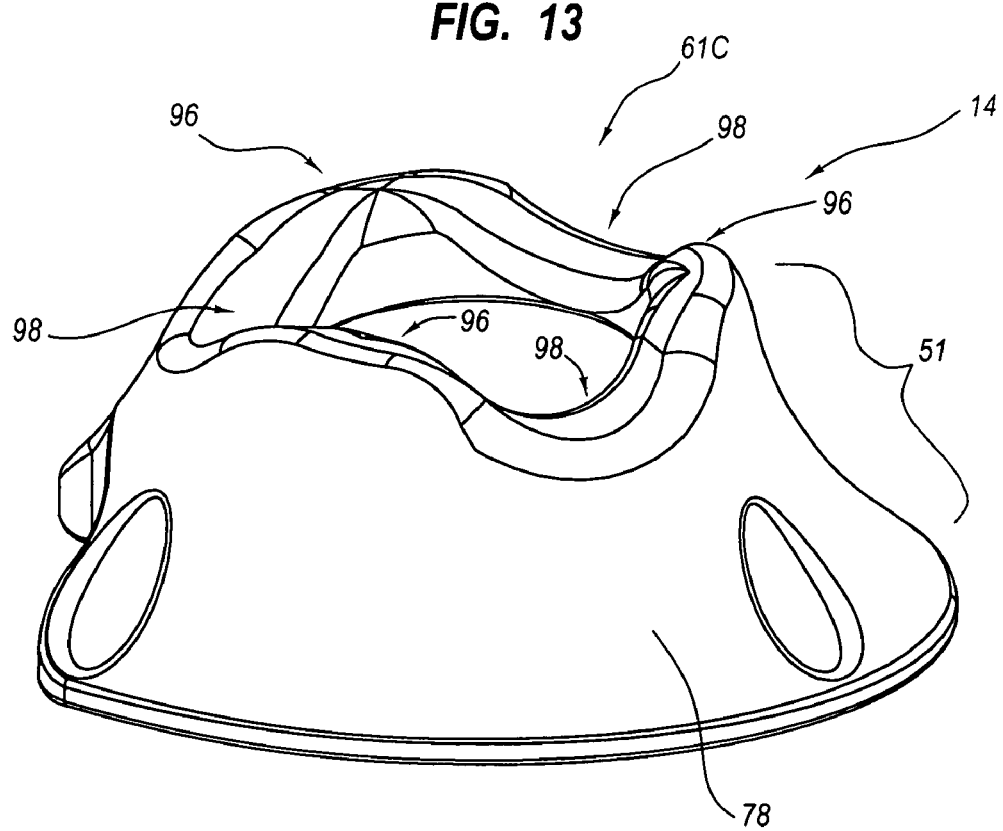
FIG. 14 shows a simplified perspective view of a cap for forming an access port according to the instant disclosure.

FIG. 13 shows a perspective view of an additional embodiment of an cap 14 for forming an access port contemplated by the instant disclosure including an upper topography 61C including circumferentially extending protrusions 80T and circumferentially extending recesses 82T, wherein transition regions 81 are provided between circumferentially extending protrusions 80T and circumferentially extending recesses 82T. Such transition regions 81, as shown in FIG. 13, may taper or generally smoothly transition between a circumferentially extending protrusion 80T and a circumferentially extending recess 82T. Also, FIG. 14 shows a perspective view of an additional embodiment of a cap 14 for forming an access port contemplated by the instant disclosure including an upper topography 61C including protrusion regions 96 and recessed regions 98 that transition between one another and alternate circumferentially so as to form an undulating topography comprising upper topography 61C. Such an undulating topography, as shown in FIG. 14, generally smoothly transitions between circumferentially adjacent protrusion regions 96 and recessed regions 98.

Figure 15A:
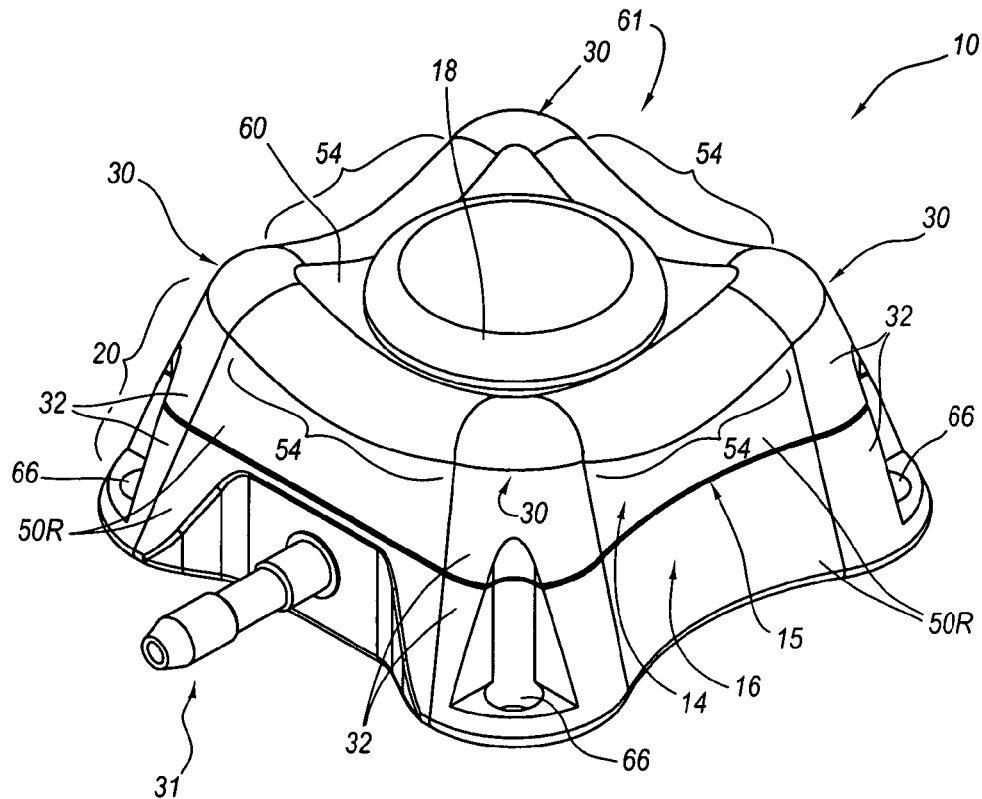
FIG. 15A shows a perspective view of an embodiment of an access port according to the instant disclosure.
Figure 15B:
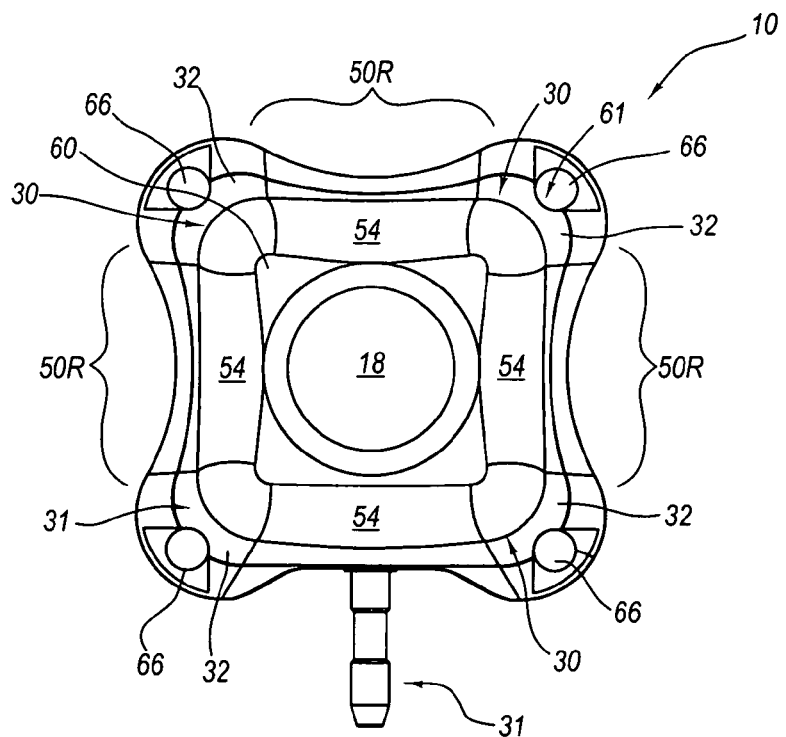
FIG. 15B shows a top elevation view of the access port shown in FIG. 15A.

In a further embodiment of an access port contemplated by the instant disclosure, FIG. 15A and 15B show a perspective view and a top elevation view, respectively, of an access port 10 generally configured as is described with reference to FIG. 5 but may include at least one nonplanar side surface. In another embodiment, access port 10 as shown in FIG. 15 may be configured as shown in FIGS. 1-4 or FIGS. 6-7, or any embodiments described hereinbelow, without limitation.

Figure 16:
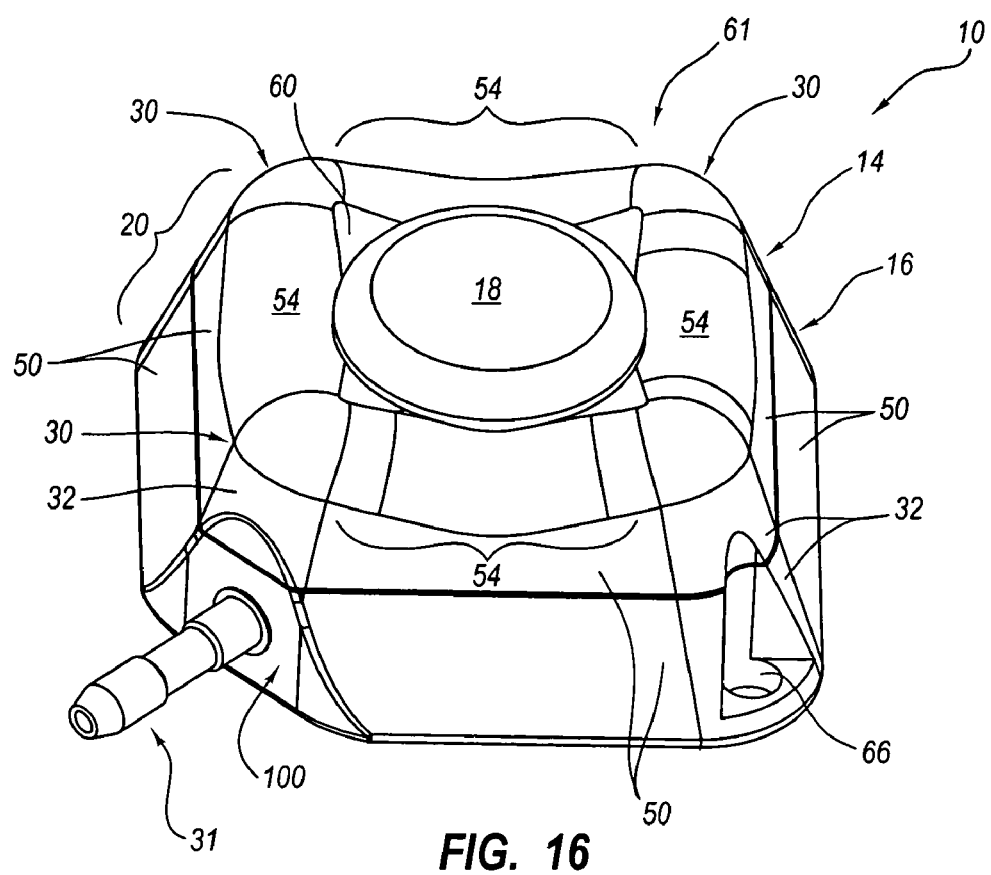
FIG. 16 shows a perspective view of an access port according to the instant disclosure.

More specifically, elongated body 20 of access port 10, as shown in FIGS. 15A and 15B, includes three side surfaces 50R that extend arcuately (as shown in FIG. 15B). Such a configuration may provide an access port 10 that is identifiable subsequent to implantation. In yet another embodiment of an access port contemplated by the instant disclosure, FIG. 16 shows a perspective view of an access port 10 including a side wall 100 that truncates a portion of a radius 32 formed between side surfaces 50 of access port 10. It may also be noted that such an access port 10 may include three suture apertures 66, which may, taken alone or in combination with at least one other feature, comprise at least one identifiable feature of an access port contemplated by the instant disclosure. In addition, as shown in FIG. 16, outlet stem 31 may extend from side wall 100.

Figure 17:
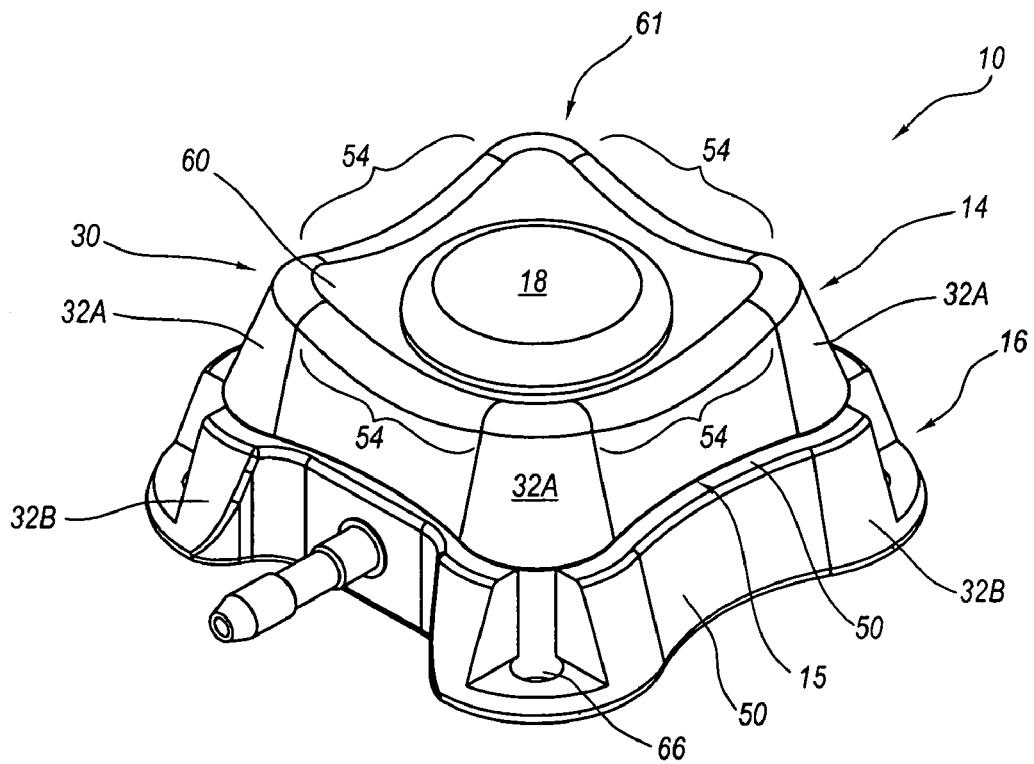
FIG. 17 shows a perspective view of an access port according to the instant disclosure.

In a further embodiment of an access port contemplated by the instant disclosure, FIG. 17 shows a perspective view of an access port 10 wherein cap 14 and base 16, when assembled to one another along mating line 15, form a flange feature or lip feature 102 that extends about at least a portion of the periphery of the access port 10. As shown in FIG. 17, lip feature 102 extends substantially about the periphery of the access port 10, proximate to the mating line 15 between cap 14 and base 16. Such a feature may comprise at least one identifiable feature of an access port contemplated by the instant disclosure. Thus, it may be appreciated that a peripheral discontinuity between the cap 14 and base 16 may be formed generally along the mating line 15 therebetween. In the embodiment of an access port as shown in FIG. 7, an overhanging rim feature 76 may comprise a peripheral discontinuity or, in the embodiment of an access port as shown in FIG. 17, a lip feature 102 may comprise a peripheral discontinuity.

Figure 18:
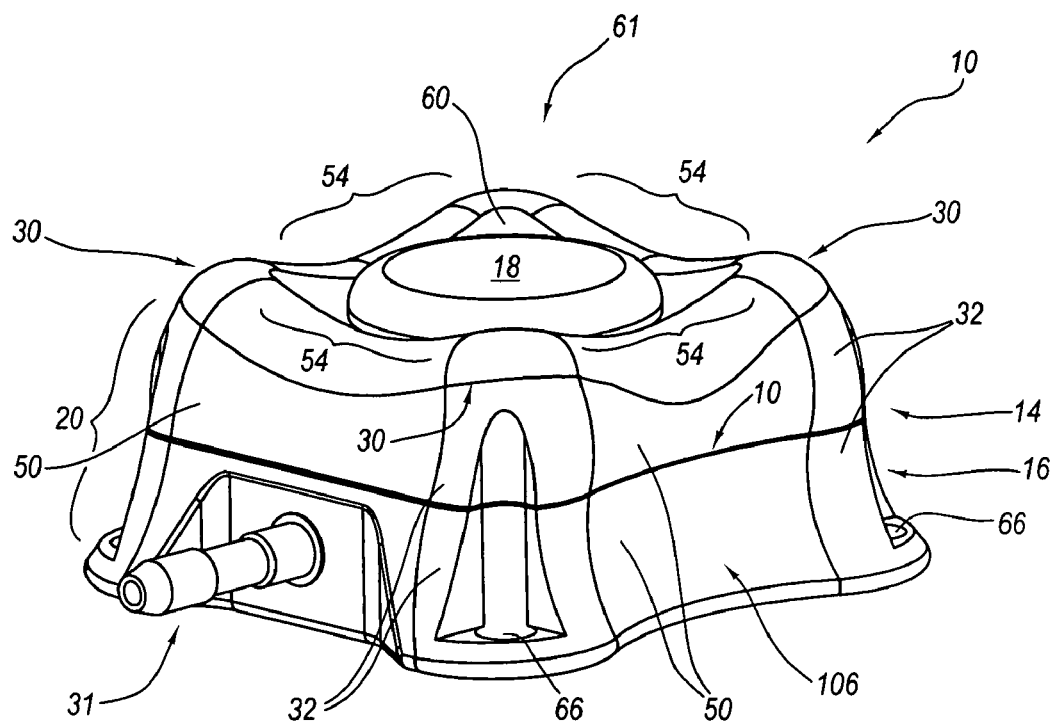
FIG. 18 shows a perspective view of an access port according to the instant disclosure.

In a further embodiment of an access port contemplated by the instant disclosure, FIG. 18 shows a perspective view of an access port 10 wherein at least a portion of at least one side surface 50 is concave. As shown in FIG. 18, concave region 106 of side surface 50 is concave. Concavity (i.e., a concave region 106) may be exhibited over at least a portion of a side surface of an access port of any of the embodiments as shown herein, without limitation. Thus, at least one side surface 50 of an access port contemplated by the instant disclosure having at least at least a portion thereof that is concave is one exemplary example of at least one perceivable feature for identification of an access port contemplated by the instant disclosure.

In a further embodiment of an access port contemplated by the instant disclosure, FIG. 18 shows a perspective view of an access port 10 wherein at least a portion of at least one side surface 50 is concave. As shown in FIG. 18, region 106 of side surface 50 is concave. Concavity may be exhibited over at least a portion of a side surface of an access port of any of the embodiments as shown herein, without limitation. Thus, at least one side surface 50 of an access port contemplated by the instant disclosure having at least at least a portion thereof that is concave is one exemplary example of at least one perceivable feature for identification of an access port contemplated by the instant disclosure.

Figure 19:
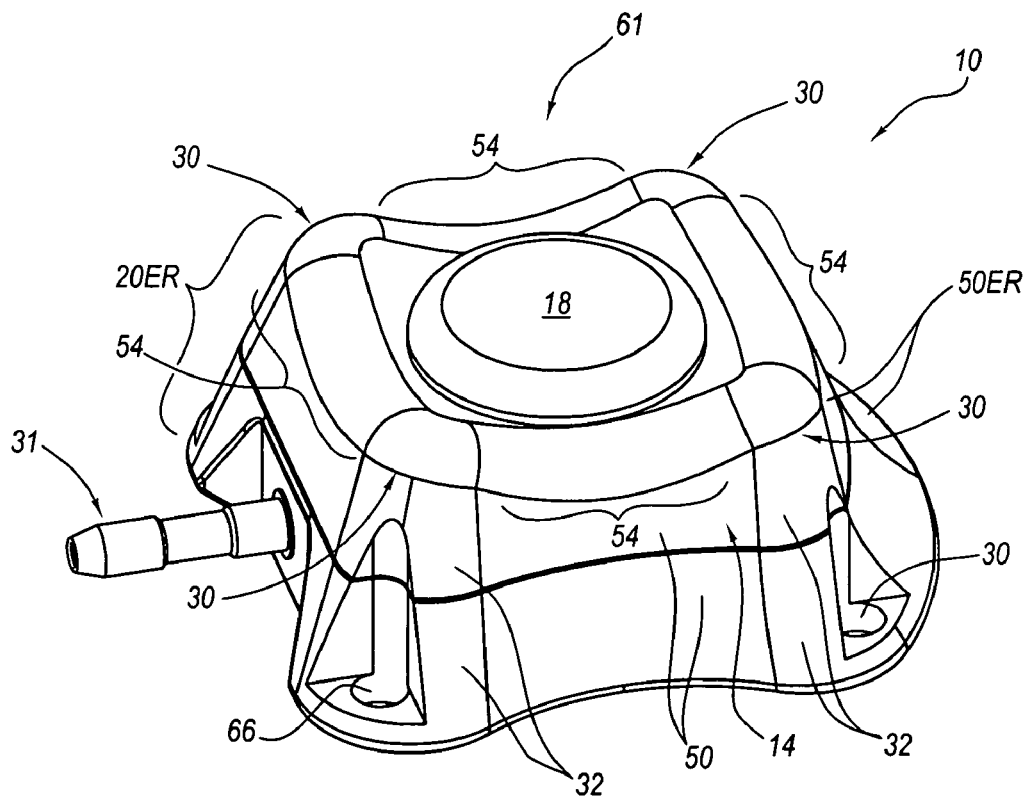
FIG. 19 shows a perspective view of an access port according to the instant disclosure.

In a further embodiment of an access port contemplated by the instant disclosure, FIG. 19 shows a perspective view of an access port 10 generally configured as is described with reference to FIG. 6A and 6B. More specifically, elongated body 20ER, as shown in FIG. 19 includes a side surface 50ER that extends arcuately from upper topography 61 of access port 10 downwardly (i.e., toward reference plane 11 as shown in FIGS. 1A and 1B). Such a configuration may provide an elongated body 20E of an access port 10 having an elongated side portion.

It should be understood from the above-described various embodiments of an access port contemplated by the instant disclosure that many variations, additions, or different features may be encompassed by the instant disclosure. Thus, the instant disclosure is not limited to the several above-described exemplary embodiments.

Figure 20:
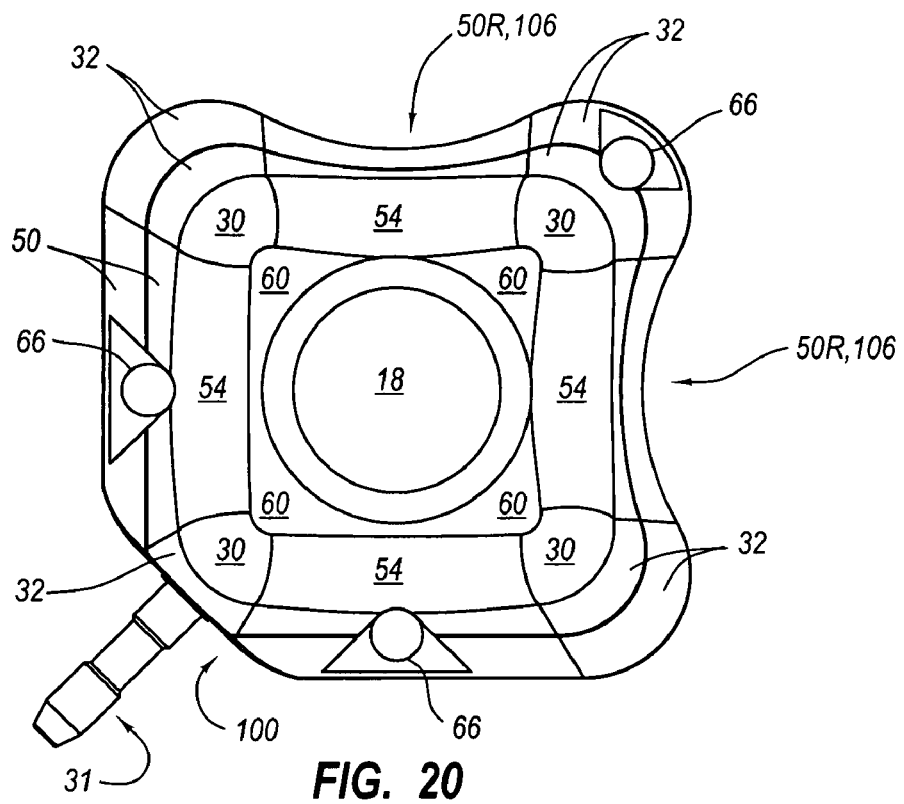
FIG. 20 shows a perspective view of an access port according to the instant disclosure.

For example, as shown in FIG. 20, which shows a top elevation view of an access port 10 contemplated by the instant disclosure, an access port 10 may include a side wall 100 that at least partially truncates a radius 32 between side surfaces 50, outlet stem 31 extending from side wall 100, and at least one of a concave region 106 and an arcuate surface 50R. Further, as shown in FIG. 20, suture apertures 66 may be positioned so as to identify the access port 10 after subcutaneous implantation.

Figure 21:
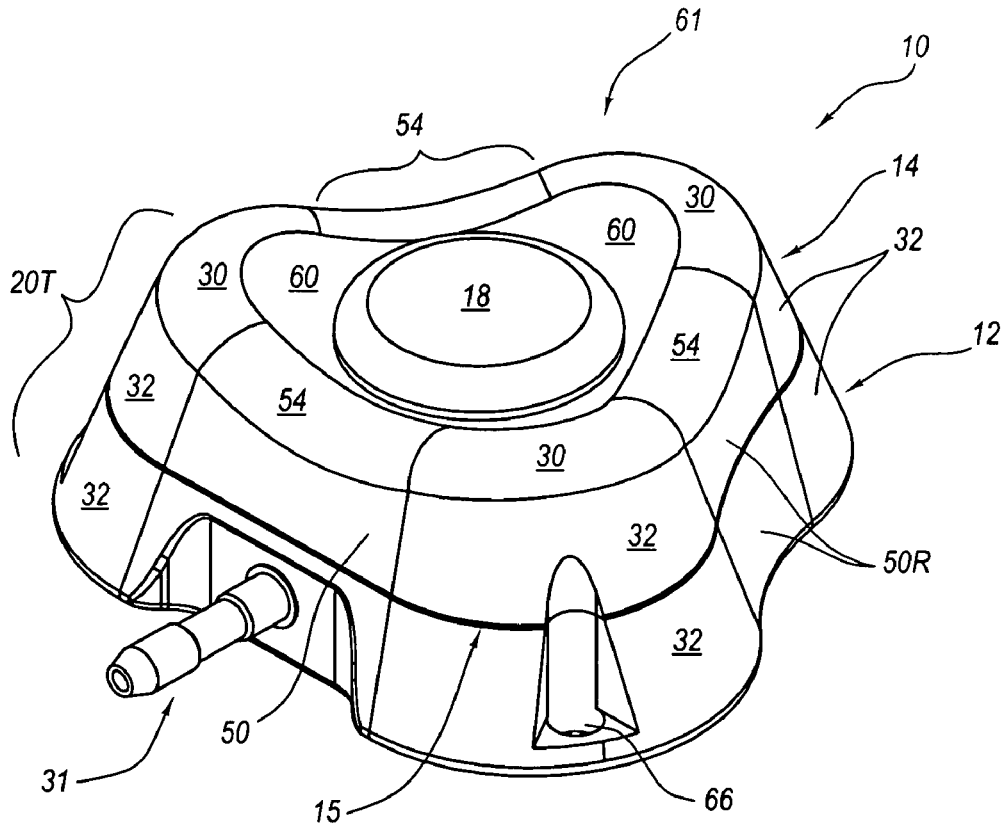
FIG. 21 shows a perspective view of an access port according to the instant disclosure.

Additionally, the instant disclosure contemplates access ports having an exterior geometry that is polygonal in nature. Specifically, the instant disclosure contemplates that an access port contemplated by the instant disclosure may exhibit a generally triangular exterior. Thus, as shown in FIG. 21, body 20 may exhibit a generally pyramidal or tapered shape (i.e., a polygonal base having surfaces for each side of the polygon extending toward a common vertex). Generally, a body 20T of an access port 10 may extend between a generally triangularly-shaped base and a relatively smaller, generally triangularly-shaped upper base. Accordingly, the exterior of access port 10 may be substantially defined by three side surfaces (e.g., 50, 50R, 102, 50E) having radiuses 32 extending therebetween. In addition, the upper topography 61 of access port 10 may be defined by upper surface 60 in combination with side regions 54 and rounded corner regions 30. Such a configuration may provide an access port having at least one feature that may be perceived by palpation.

Figure 22:
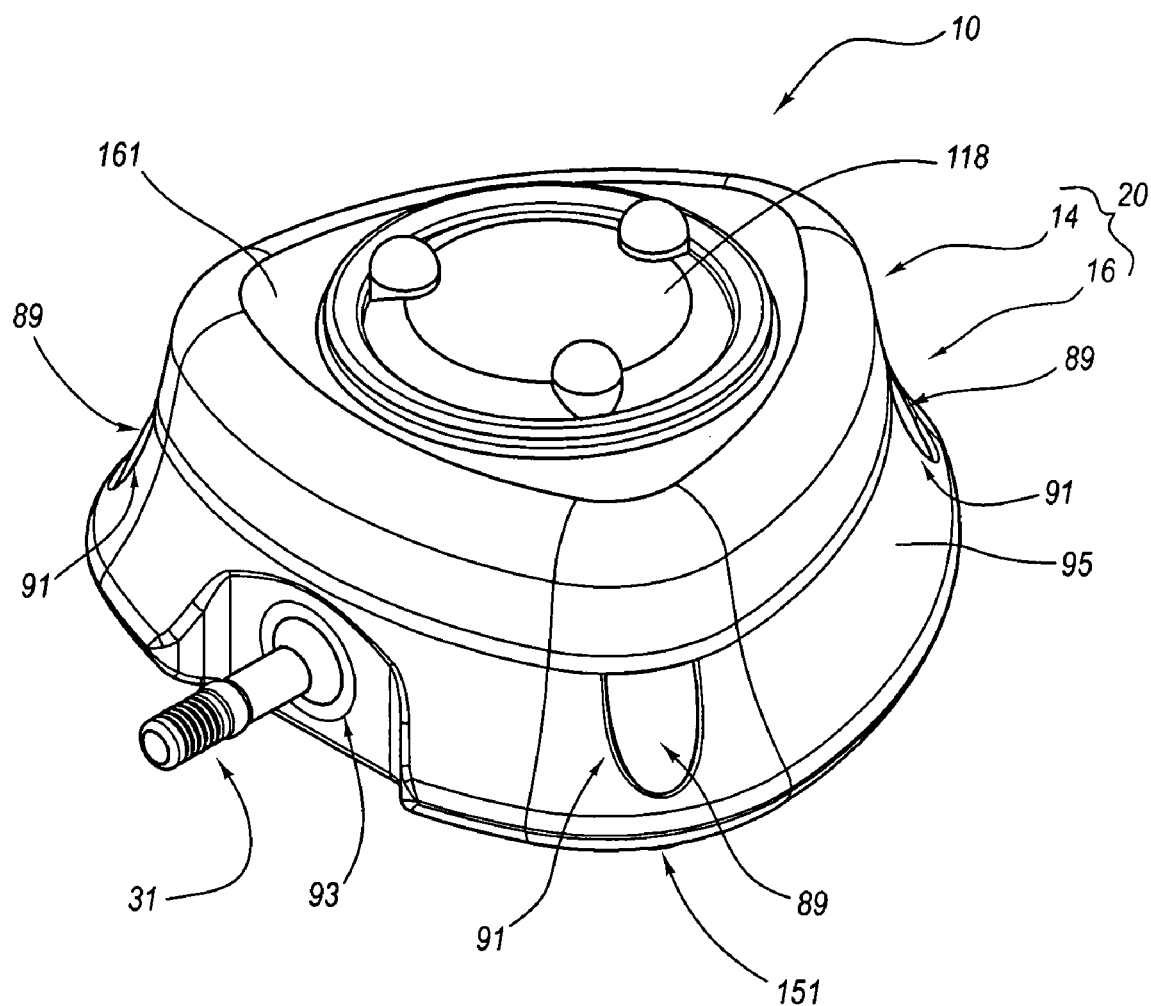
FIG. 22 shows a perspective view of another embodiment of an access port according to the instant disclosure.
Figure 23:
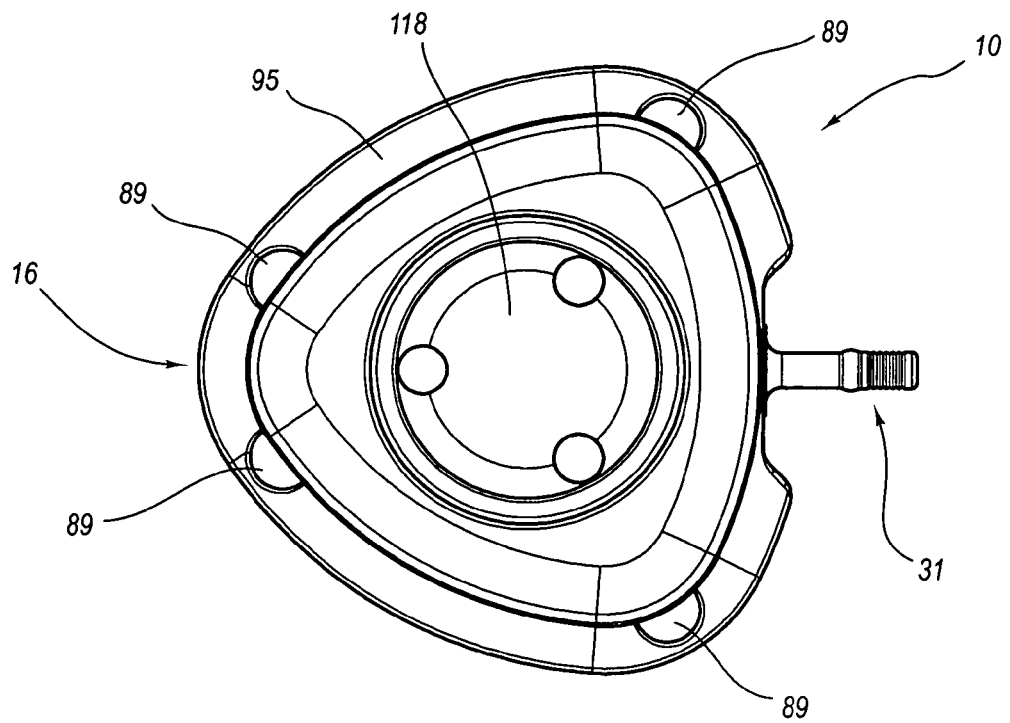
FIG. 23 shows a top elevation view of the assembled access port shown in FIG. 22.

FIGS. 22 and 23 show a perspective view and a top elevation view of another embodiment of an access port including a generally triangular exterior geometry. More particularly, as shown in FIGS. 22 and 23, a cap 14 and base 16 (collectively forming a housing) may capture a septum 118 to form an access port 10. Further, outlet stem 31 may include a stem base that may be positioned within and sealed to an outlet recess 93 formed within base 16. The outlet stem 31 may be in fluid communication with a cavity formed within the access port 10. Optionally, suture plugs 89 may be positioned within suture cavities 91 formed in base 16. Suture plugs 89 may comprise a pliant material (e.g., silicone, rubber, etc.) that may provide some resilience between sutures coupling the access port 10 (i.e., the base 16) to a patient. In further detail, a side periphery 95 (e.g., one or more side walls) of access port 10 may be generally triangular. Thus, cap 14 and base 16 may collectively form a generally triangular housing or body of access port 10. Also, the instant disclosure contemplates that side periphery 95 may increase or decrease in cross-sectional size (e.g., by tapering or arcuately transforming) between upper surface 161 of cap 14 and lower surface 151 of base 16. As shown in FIGS. 22 and 23, a transverse cross section (taken in a selected plane substantially parallel to lower surface 151 of base 16) of access port 10 may be larger proximate to lower surface 151 of base 16 and may be relatively smaller proximate upper surface 161 of cap 14.

Figure 24:
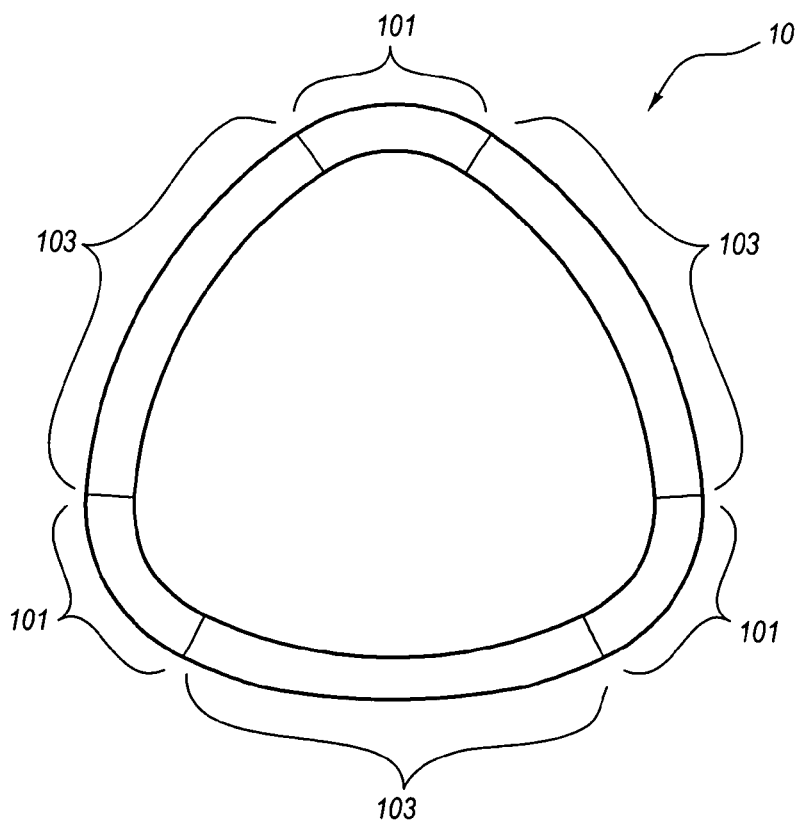
FIG. 24 shows a simplified representation of a transverse cross section of the access port shown in FIGS. 22 and 23.
Figure 25:
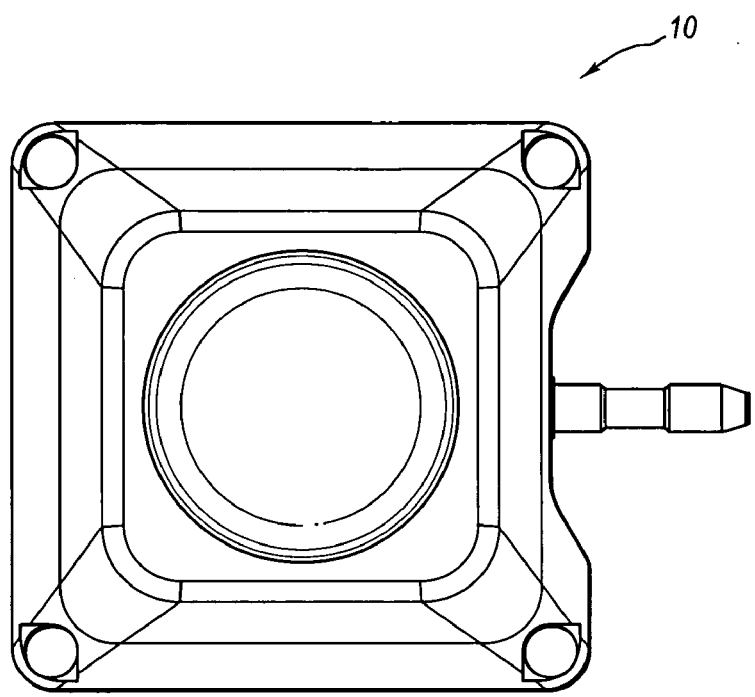
FIGS. 25-51 show perspective views of additional embodiments of an access port.
Figure 26:
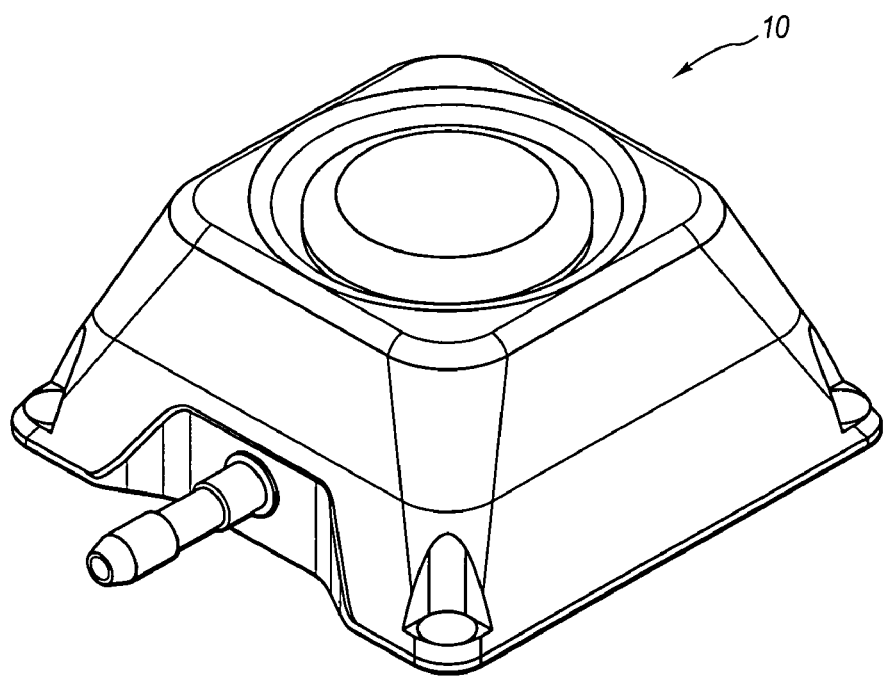
Figure 27:
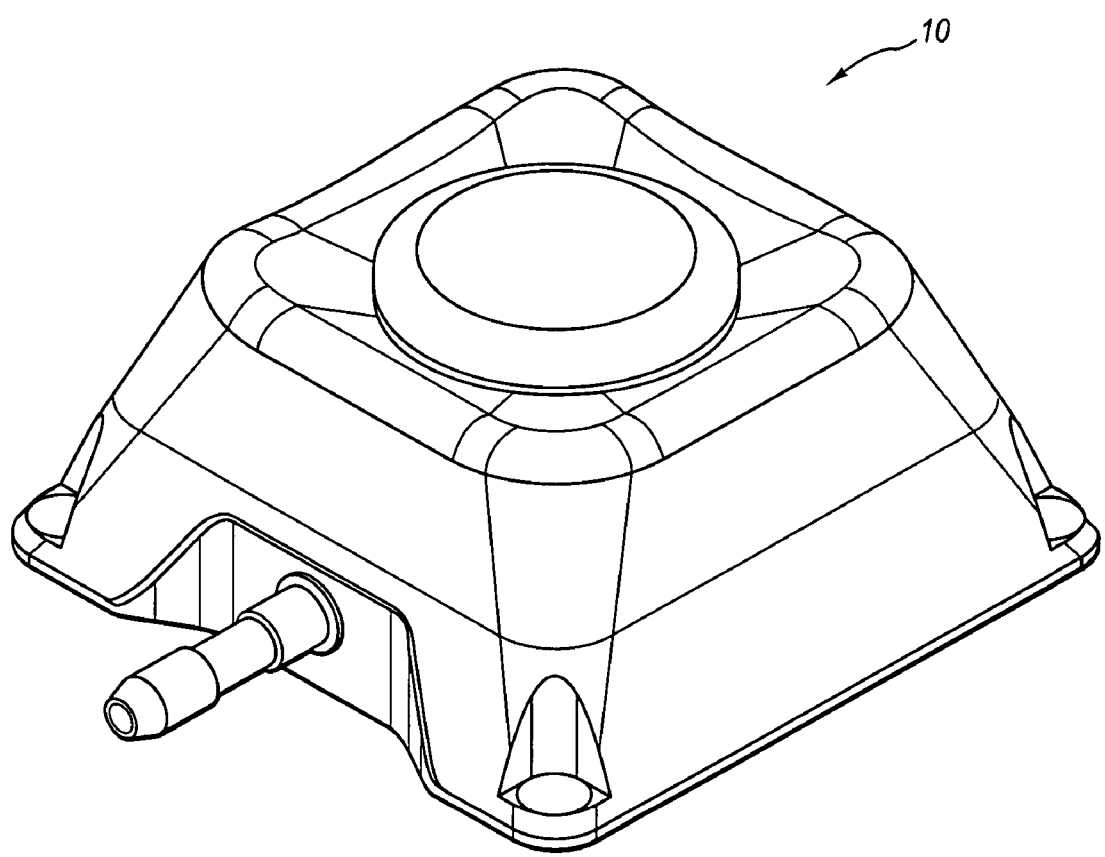
Figure 28:
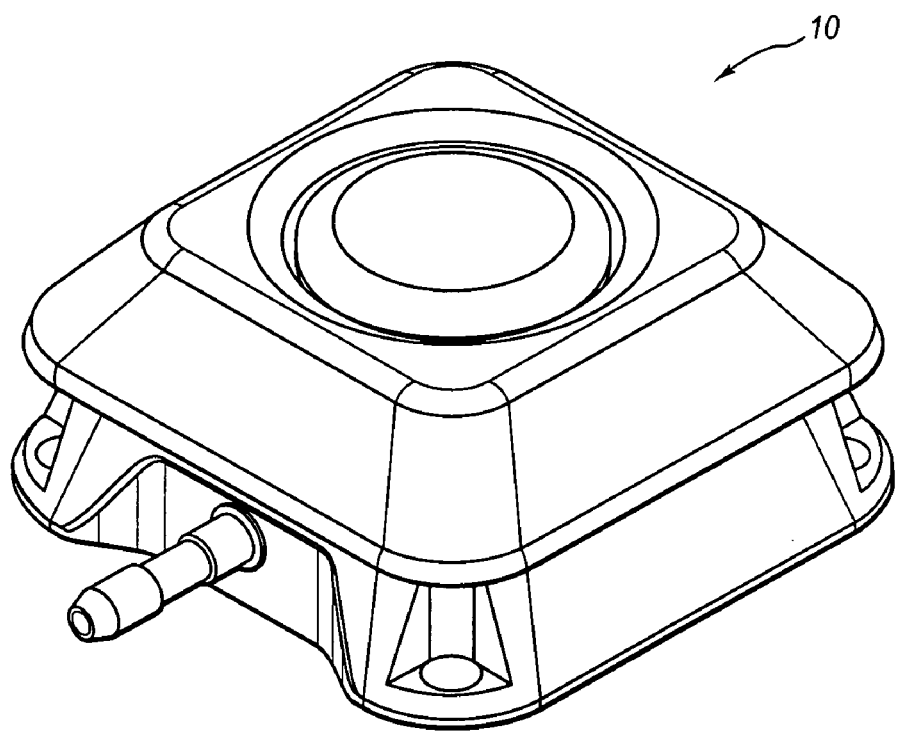
Figure 29:
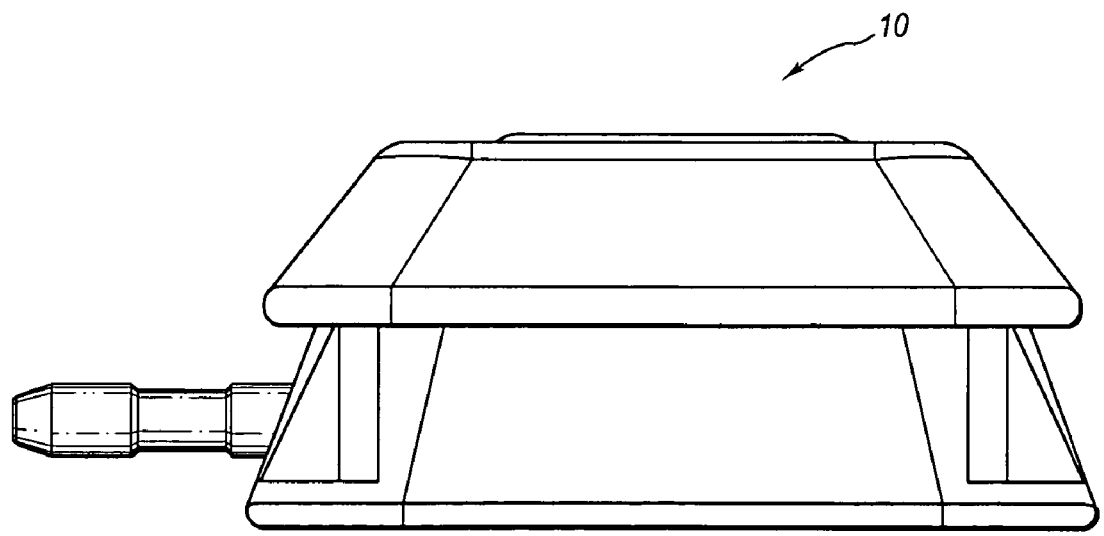
Figure 30:
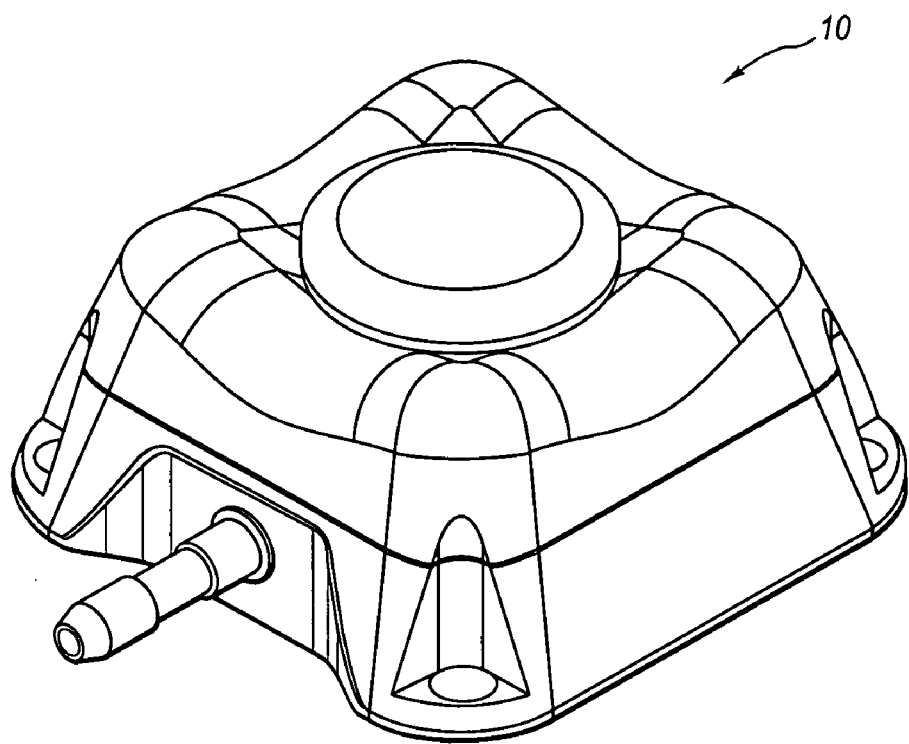
Figure 31:
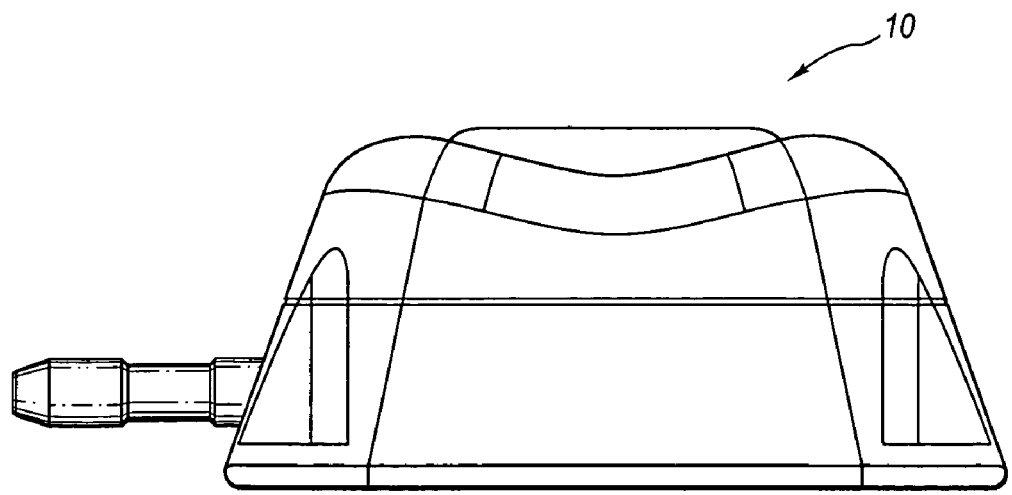
Figure 32:
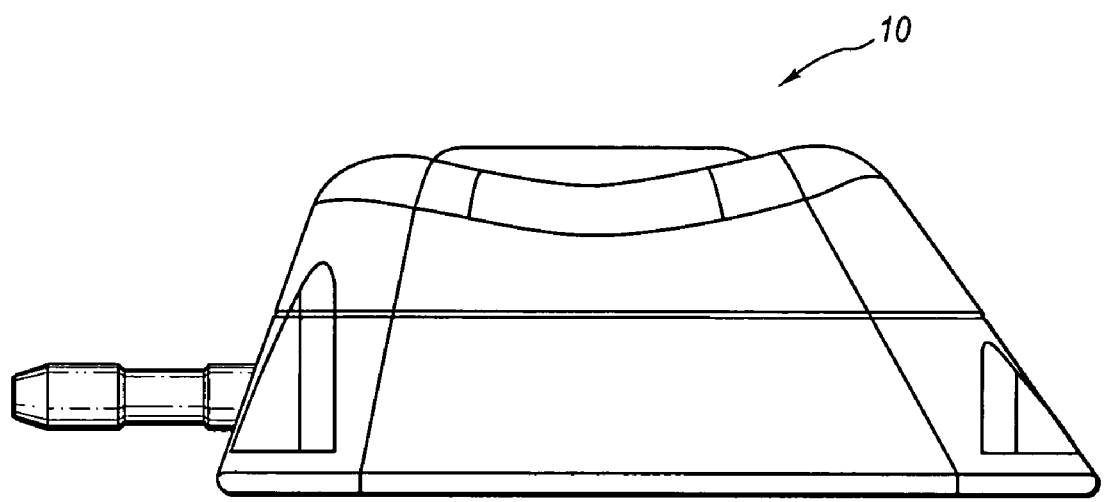
Figure 33:
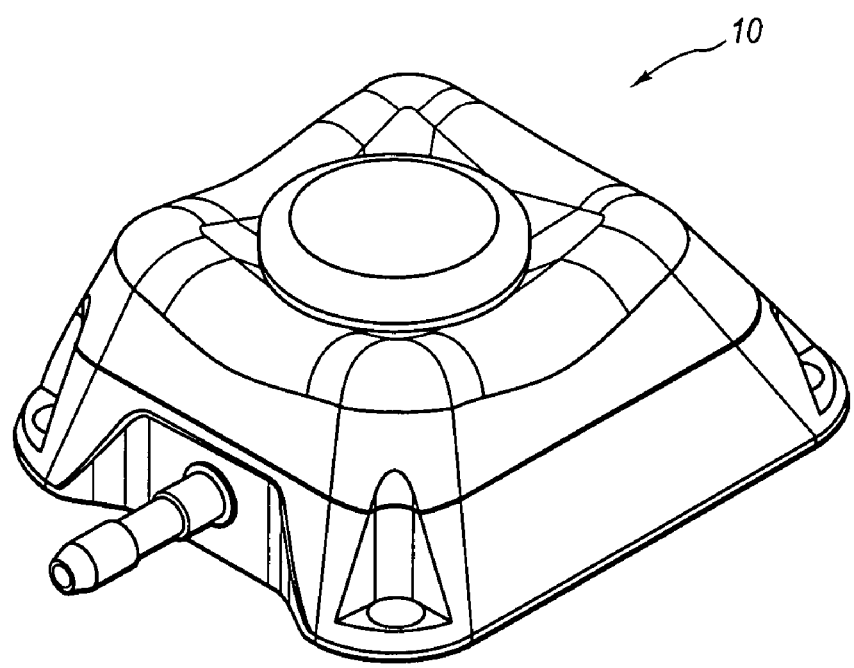
Figure 34:
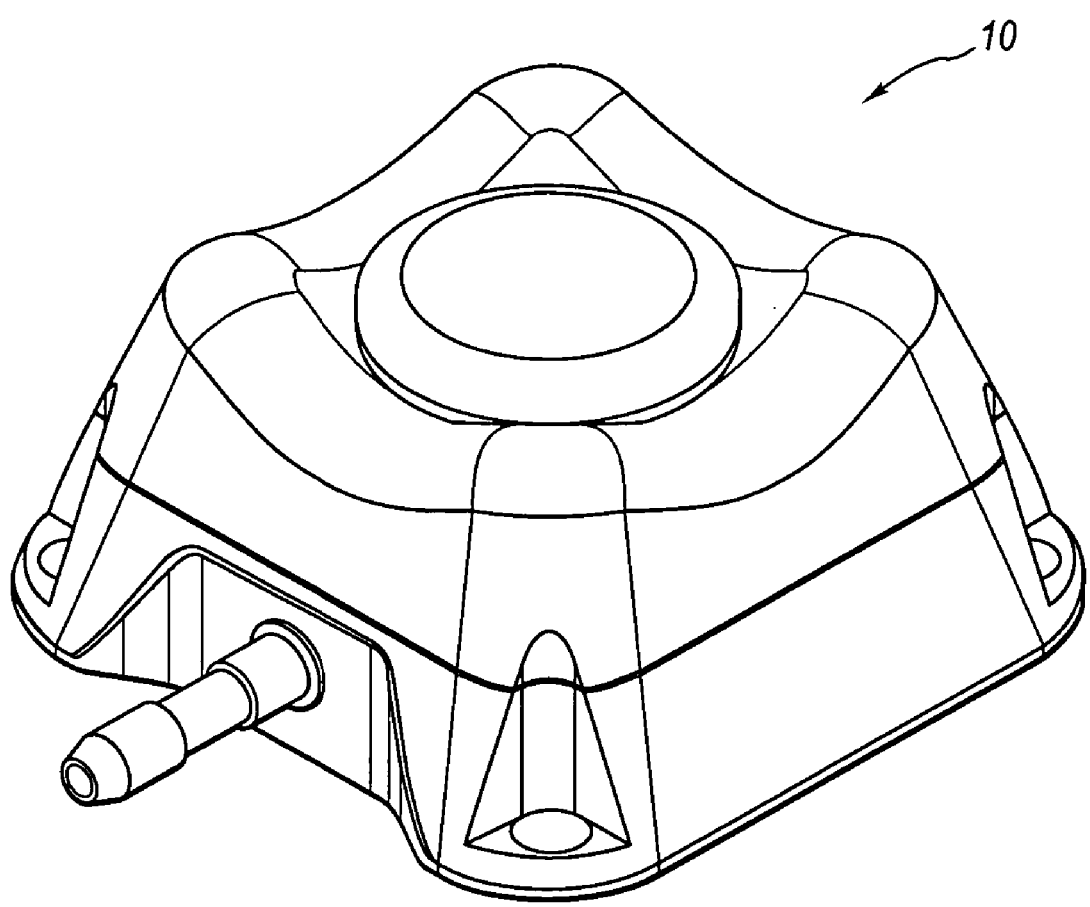
Figure 35:
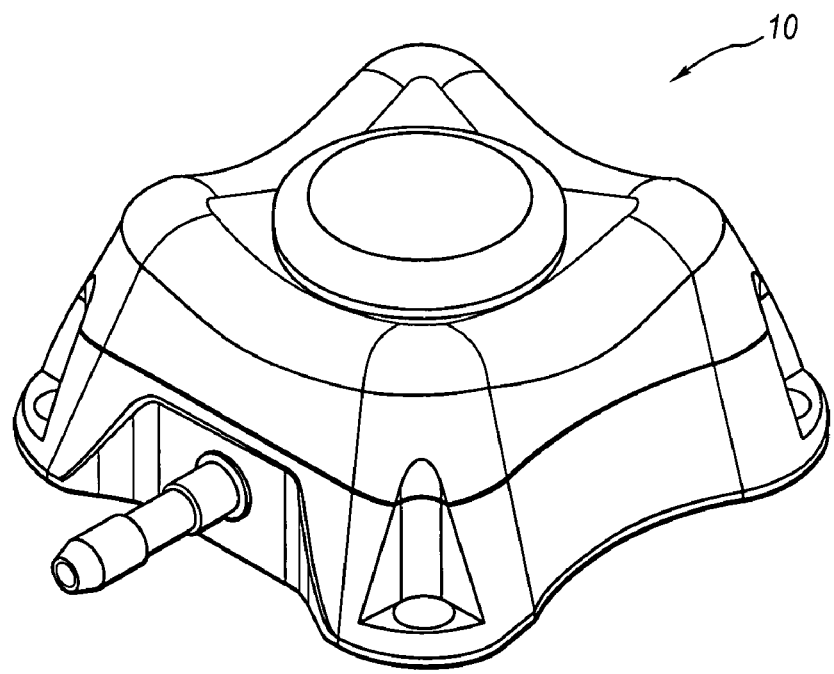
Figure 36:
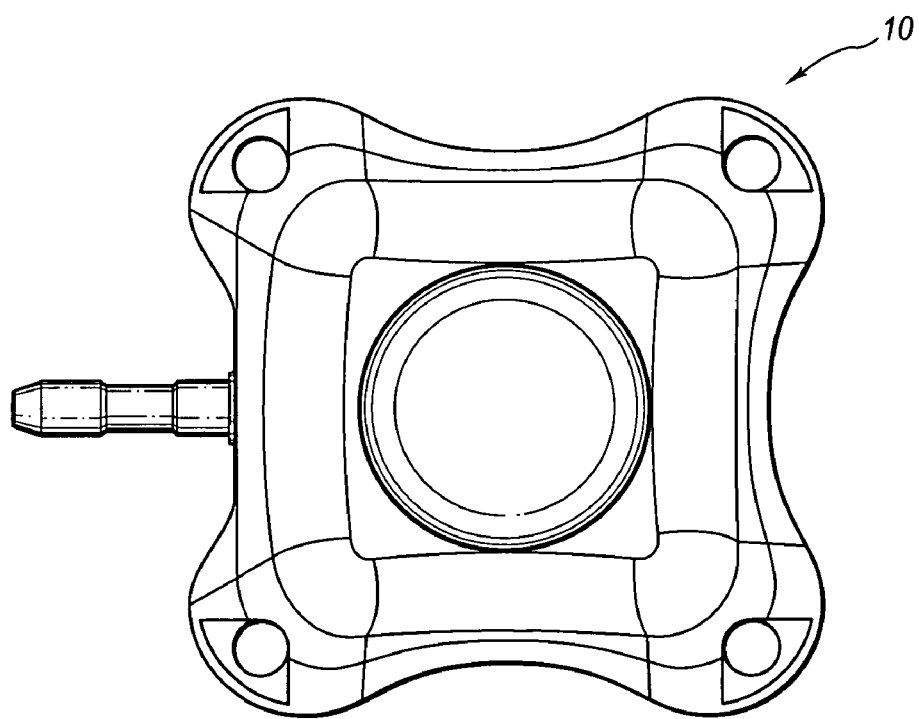
Figure 37:
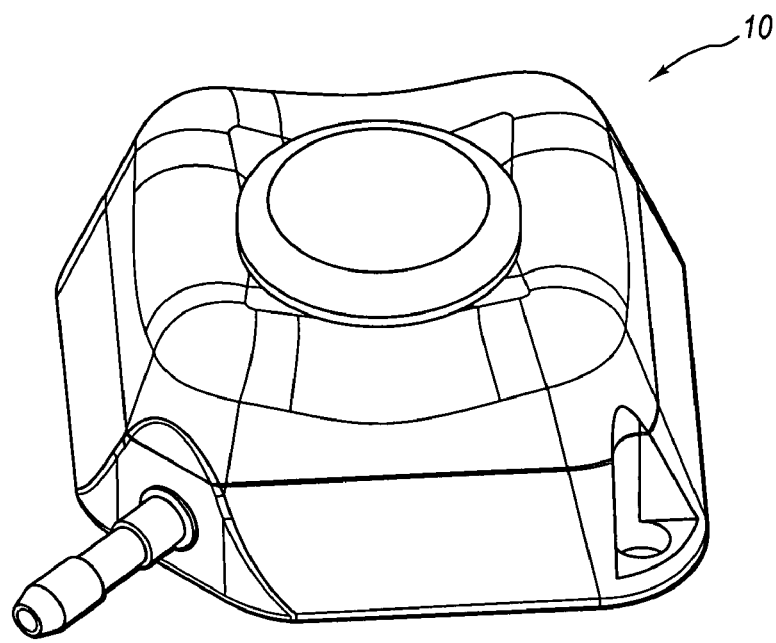
Figure 38:
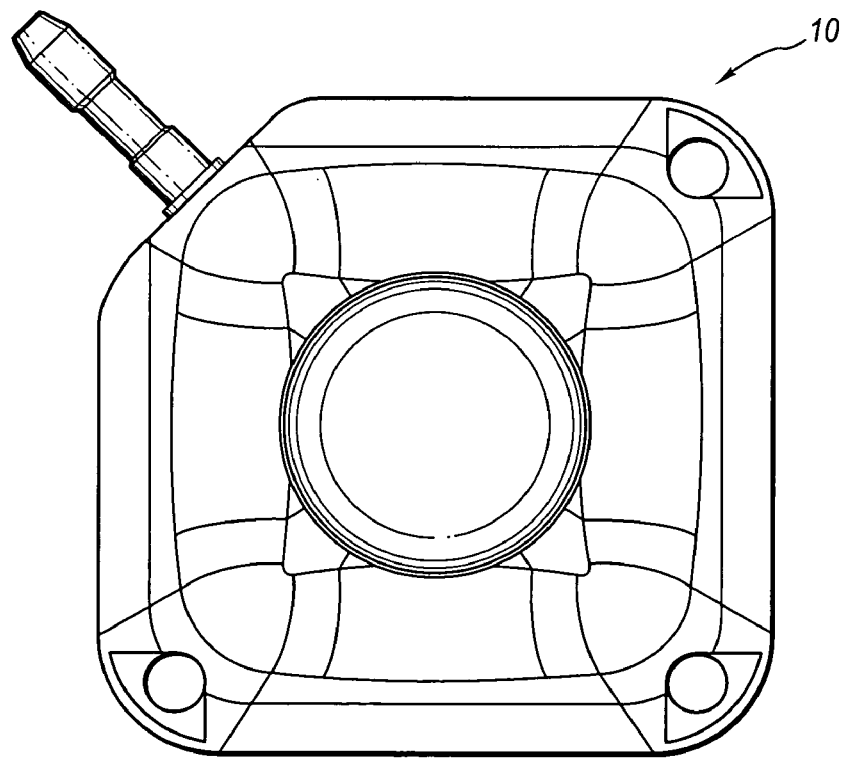
Figure 39:
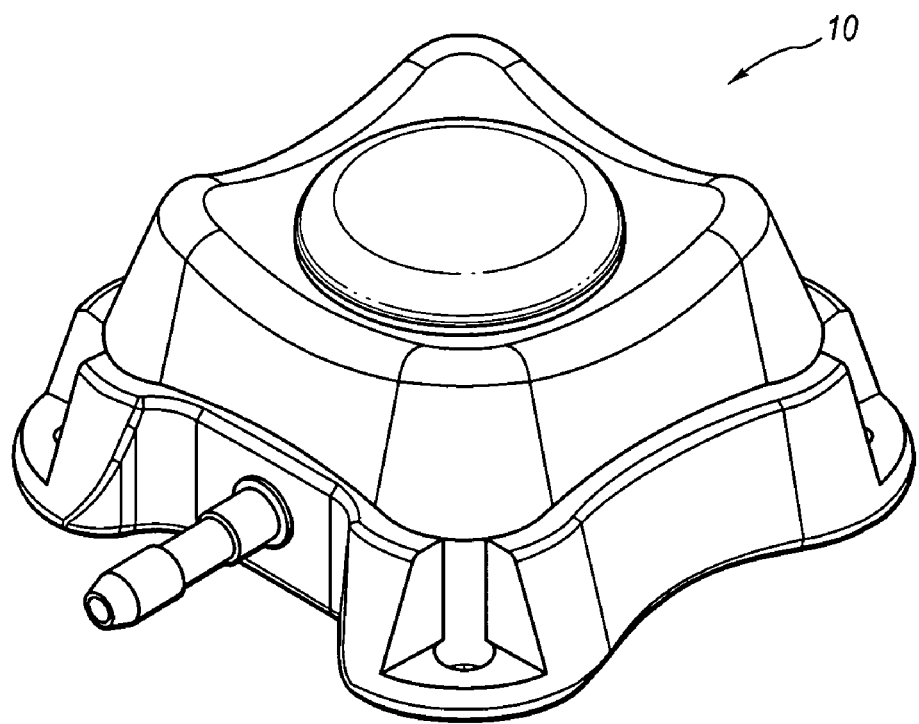
Figure 40:
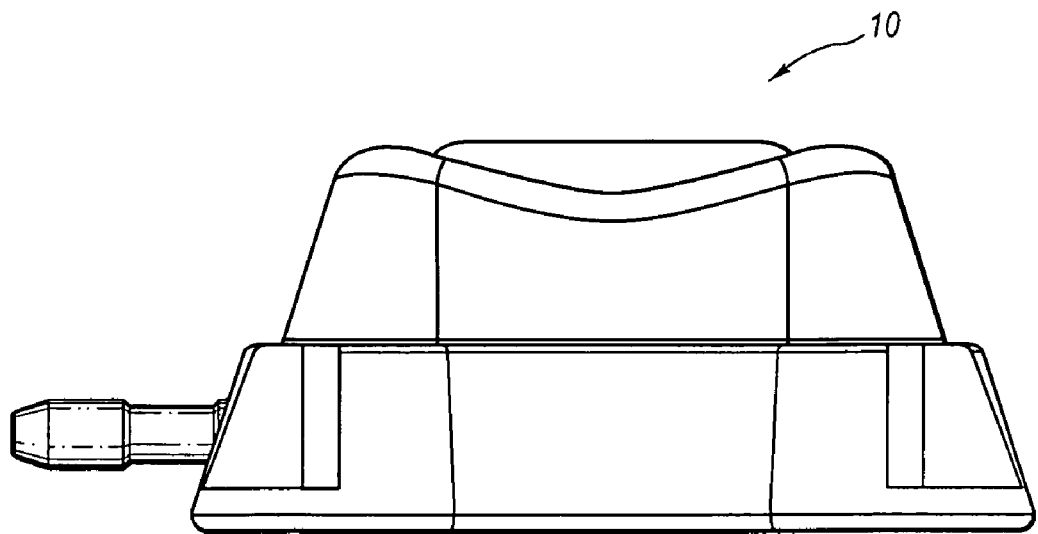
Figure 41:
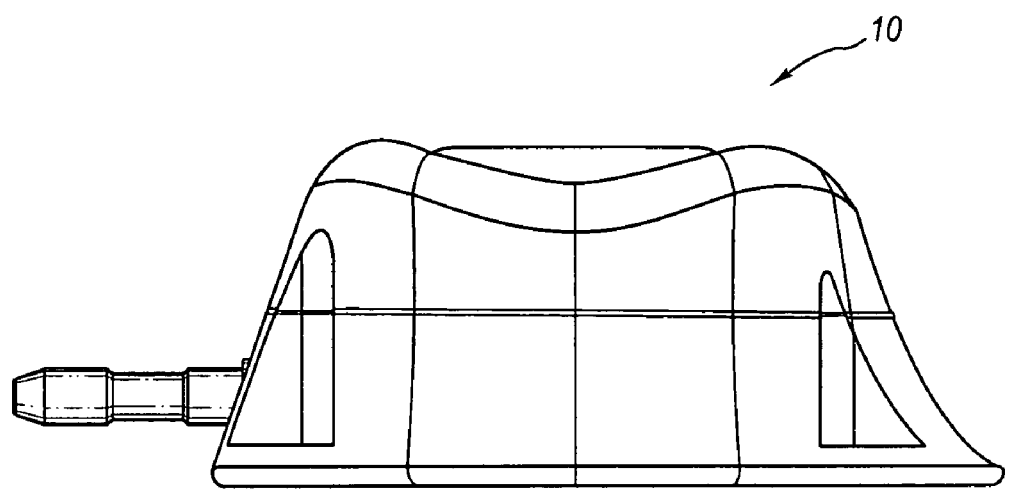
Figure 42:
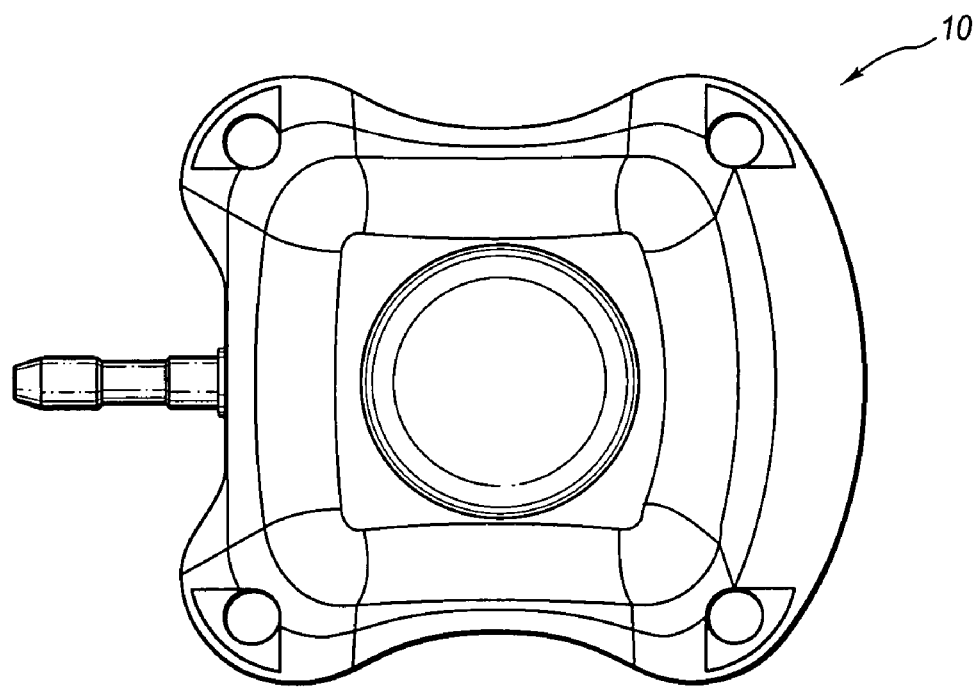
Figure 43:
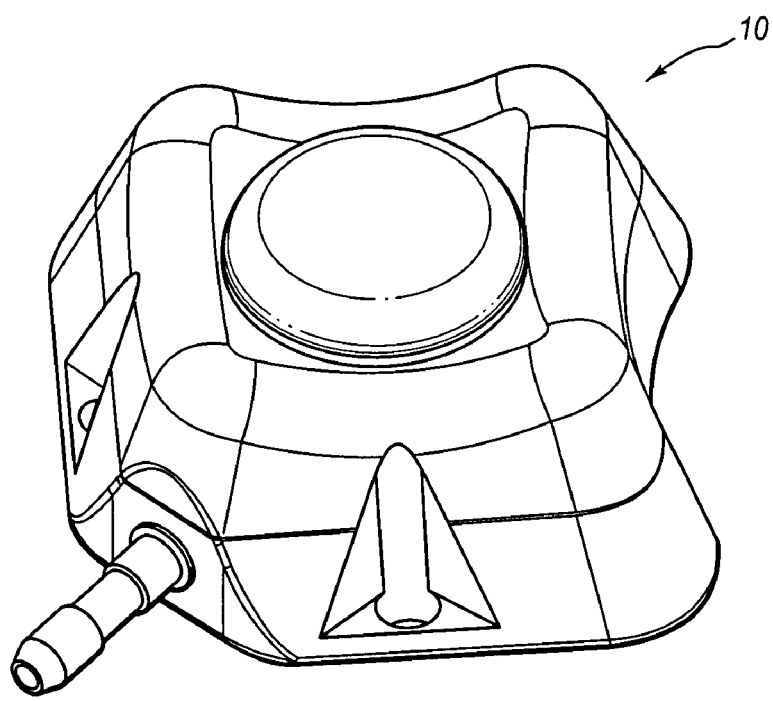
Figure 44:
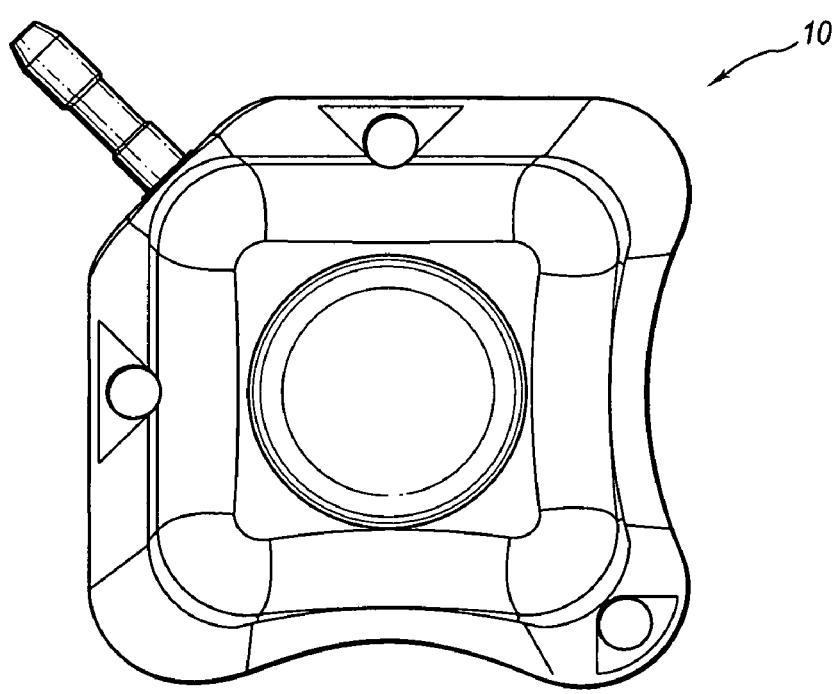
Figure 45:
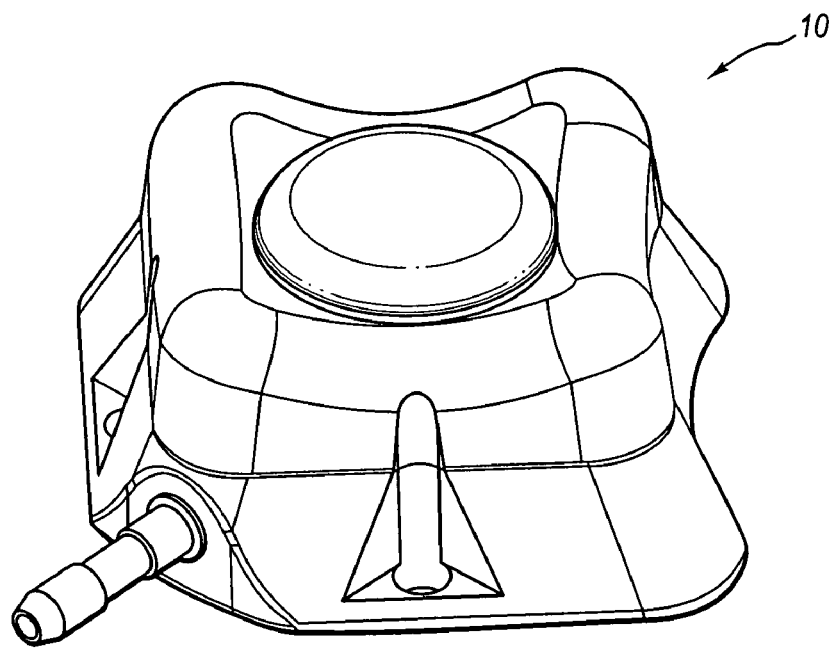
Figure 46:
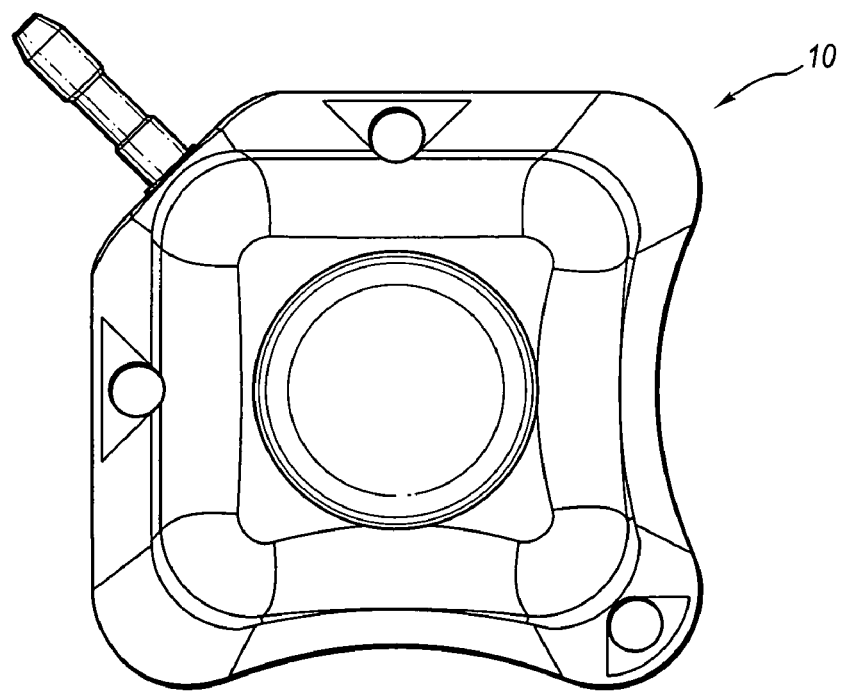
Figure 47:
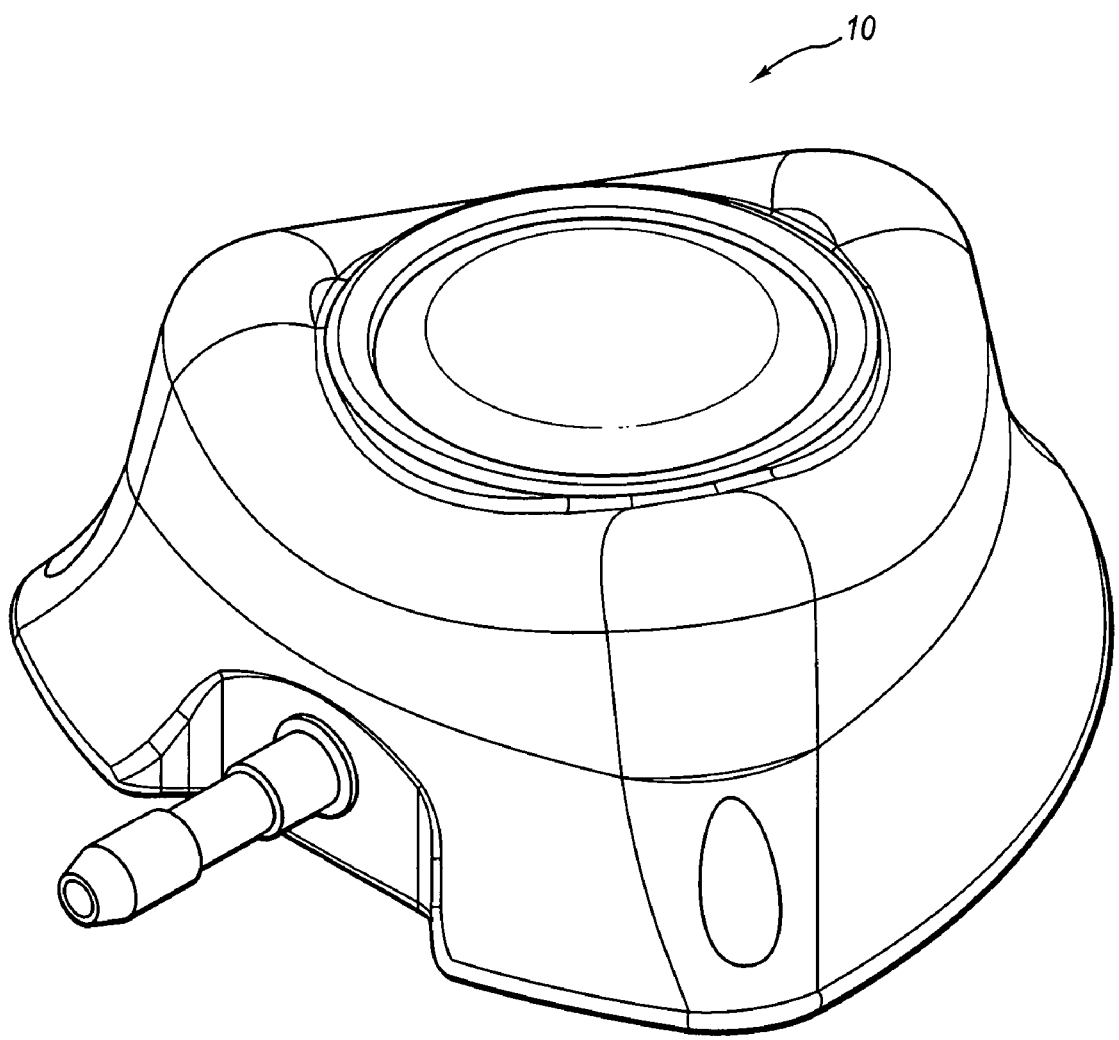
Figure 48:
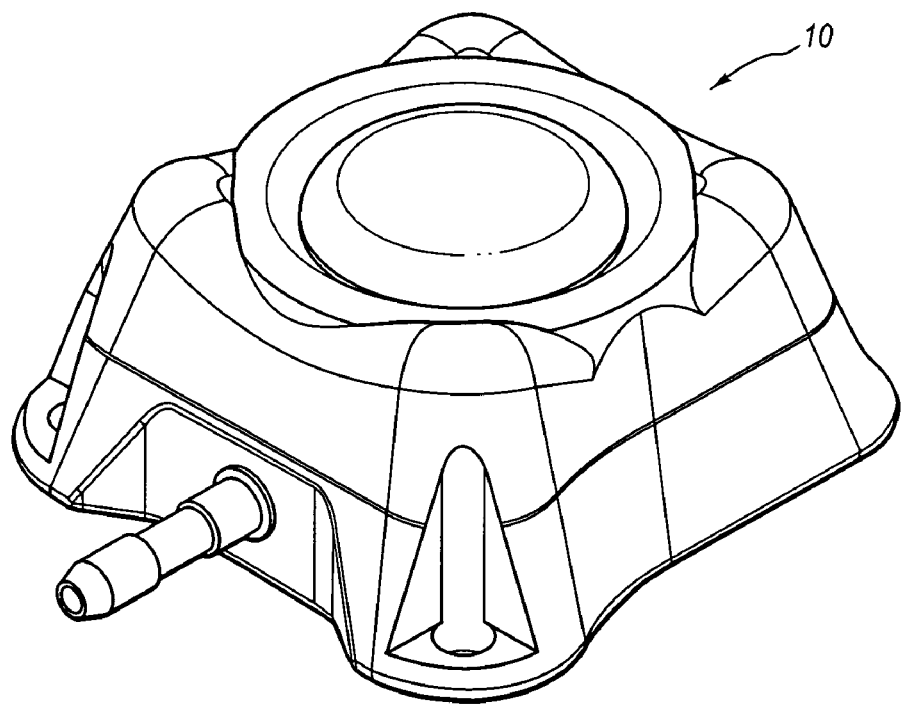
Figure 49:
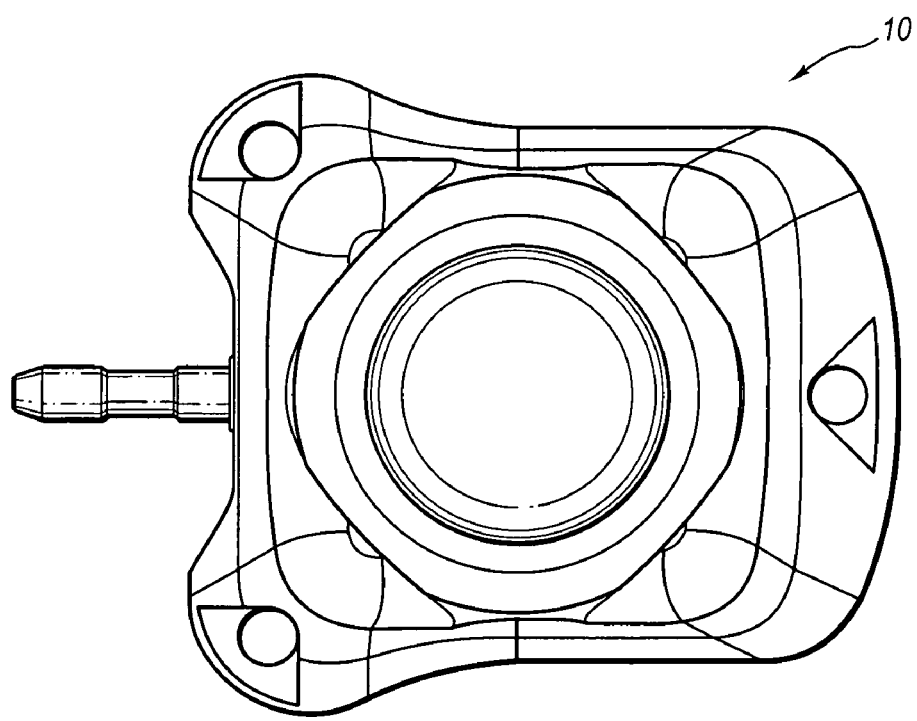
Figure 50:
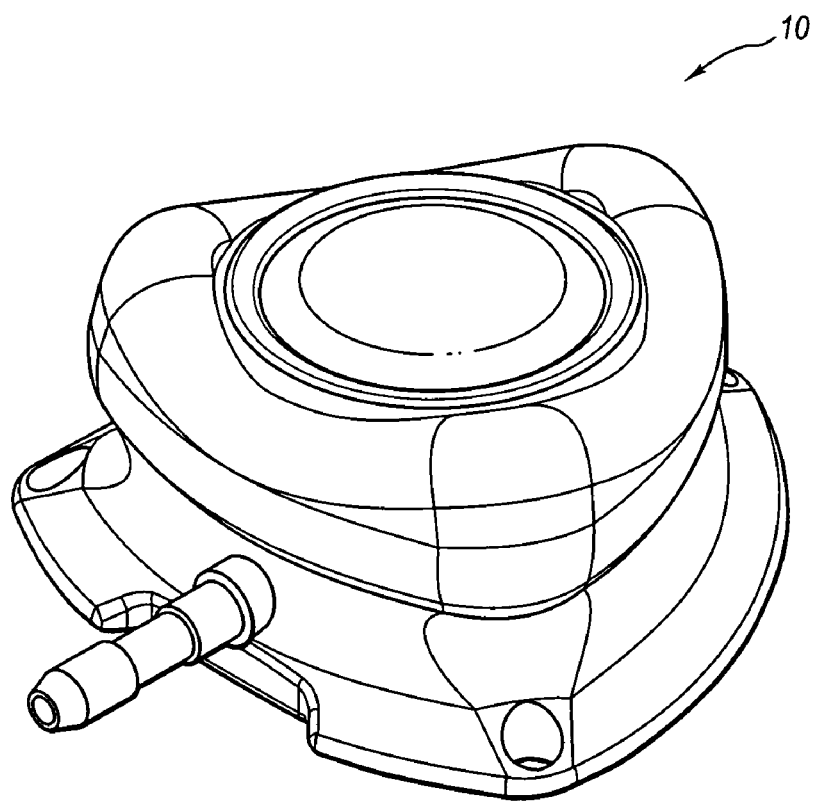
Figure 51:
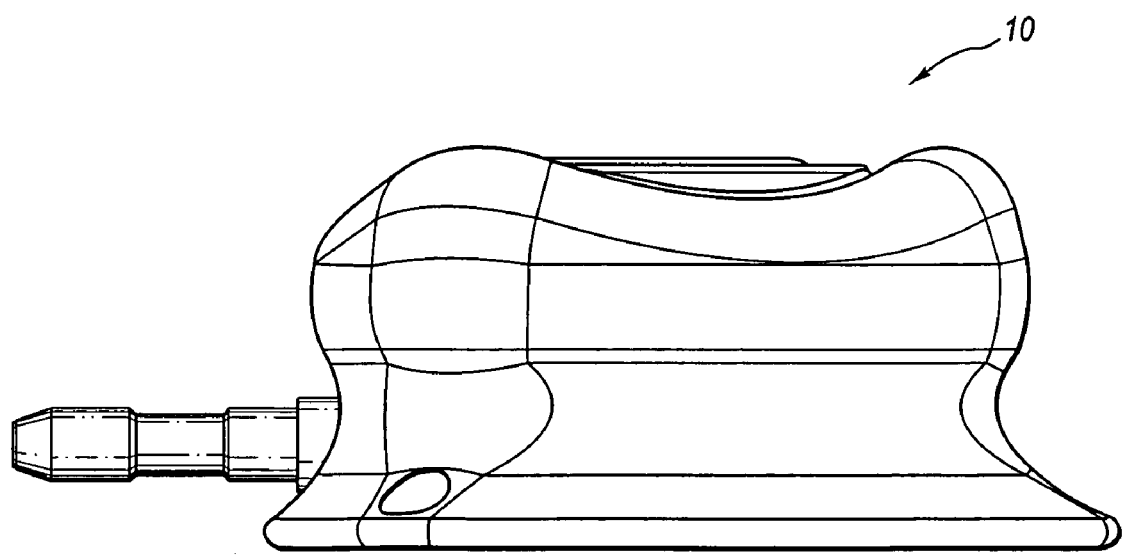

Additionally, FIG. 24 shows a simplified representation of a transverse cross section of access port 10. As shown in FIG. 24, side periphery 95 of access port 10 may define three side regions 103 that extend between associated vertex regions 101. In addition, in one embodiment and as shown in FIG. 24, side periphery 95 may define a substantially equilateral generally triangular shape. As one of ordinary skill in the art will appreciate, side regions 103 may arcuately extend between associated vertex regions 101; thus, side regions 103 may form "sides" of a generally triangular shape. Further, although vertex regions 101 are rounded, it may be appreciated that such vertex regions 101 form an intersection between adjacent side regions 103. Accordingly, one of ordinary skill in the art will appreciate that the phrase "generally triangular," as used herein, encompasses any generally three-sided geometry wherein adjacent sides intersect, without limitation. For example, the phrase "generally triangular" encompasses three sided polygons, circular triangles, equilateral triangles, etc., without limitation.

The instant disclosure also contemplates that at least one feature of an access port contemplated by the instant disclosure may not be observable visually or by palpation but, rather, may be otherwise observable. For example, the instant disclosure contemplates that at least one feature of an access port may be observable through interaction with an imaging technology such as x-ray or ultrasound. For example, in one embodiment, a metal feature (e.g., a plate or other metal geometry) may be included by an access port contemplated by the instant disclosure. As may be appreciated, such a metal feature may be represented on an x-ray generated by exposure of the access port to x-ray energy while simultaneously exposing x-ray sensitive film to x-ray energy passing through the access port. Further, the instant disclosure contemplates that a size, shape, or both size and shape of a metal feature of an access port may be configured for enhancing identification of an access port. For example, assuming that a metal feature comprises a metal plate, a size, shape, or both may be selectively tailored for identification of an access port. Similarly, a feature of an access port contemplated by the instant disclosure may be tailored for detection via ultrasound interaction. Such a feature may comprise an exterior topographical feature. In another embodiment, such a feature may comprise a composite structure including two or more materials that form an interface surface that may be identified by ultrasound imaging.

Figure 52A:
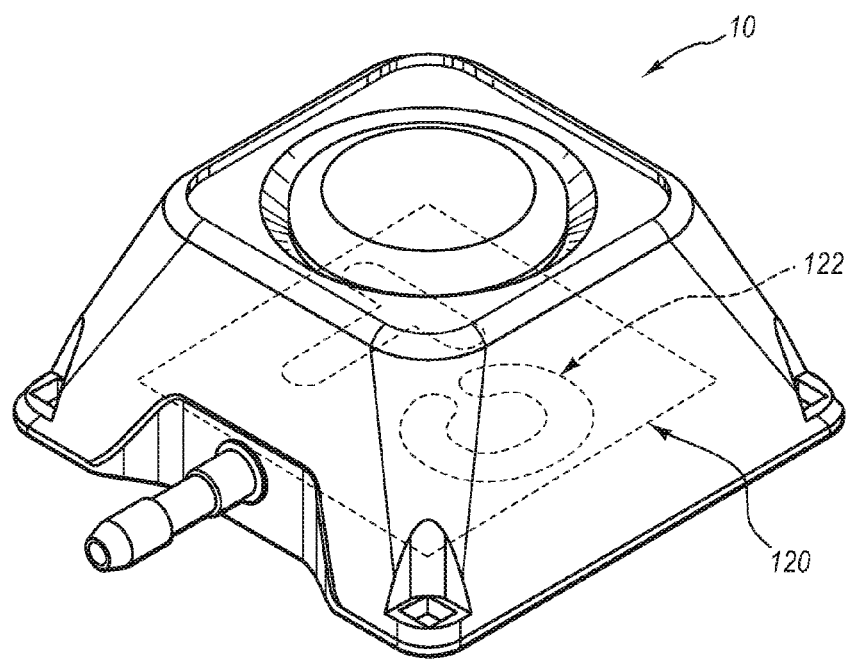
FIG. 52A shows a top perspective view of an embodiment of an access port with an alphanumeric message in the bottom of the port.
Figure 52B:
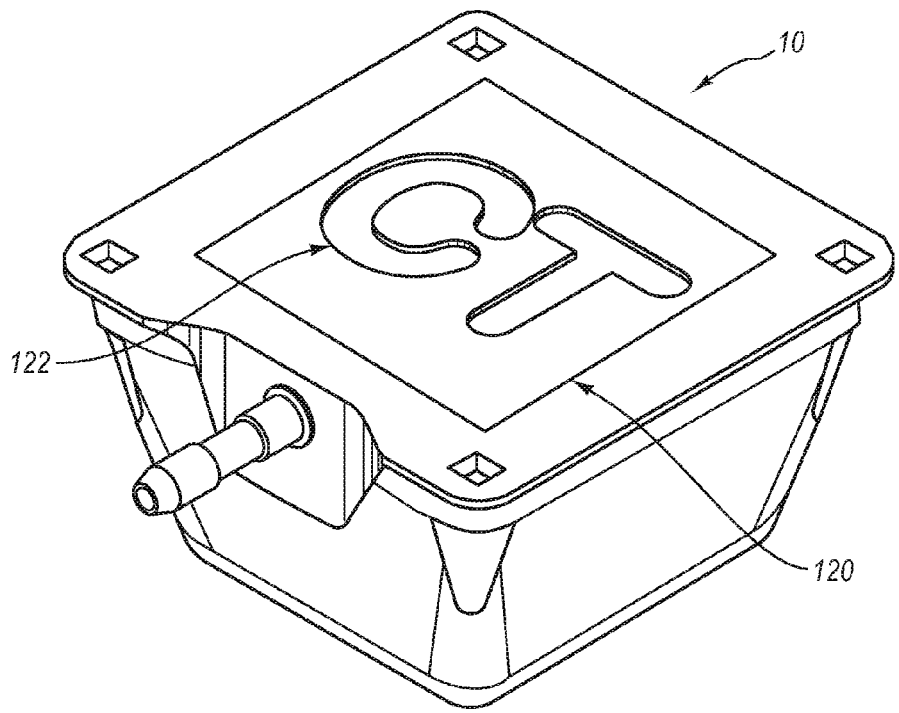
FIG. 52B shows a bottom perspective view of the embodiment in FIG. 52A.

The instant disclosure also contemplates that at least one feature of an access port contemplated by the instant disclosure may not be observable visually or by palpation but, rather, may be otherwise observable. For example, the instant disclosure contemplates that at least one feature of an access port may be observable through interaction with an imaging technology such as x-ray or ultrasound. The access port may be constructed of both metal and plastic. For example, in one embodiment, a metal feature (e.g., a plate or other metal geometry) may be included by an access port contemplated by the instant disclosure. As may be appreciated, such a metal feature may be represented on an x-ray generated by exposure of the access port to x-ray energy while simultaneously exposing x-ray sensitive film to x-ray energy passing through the access port. In another embodiment, the access port may incorporate a metal disk in the bottom of the plastic port. The disk may include an alphanumeric message etched in the port disk that would be visible on radiograph (x-ray). FIGS. 52A-B illustrate one embodiment of an alphanumeric message 122 etched in a disk or plate 120 in the bottom of a port 10. Further, the instant disclosure contemplates that a size, shape, or both size and shape of a metal feature of an access port may be configured for enhancing identification of an access port. For example, assuming that a metal feature comprises a metal plate, a size, shape, or both may be selectively tailored for identification of an access port. Additionally, by way of example, a metal port may be configured to leave a square imprint on an x-ray that could identify the port as a power-injectable port. Similarly, a feature of an access port contemplated by the instant disclosure may be tailored for detection via ultrasound interaction. Such a feature may comprise an exterior topographical feature. In another embodiment, such a feature may comprise a composite structure including two or more materials that form an interface surface that may be identified by ultrasound imaging.

In one exemplary example, it is contemplated that radio frequency identification technology may be employed for identification of an access port contemplated by the instant disclosure. Particularly, so-called active RFID tags are powered by an internal battery and are typically read/write devices. Currently, a suitable cell coupled to suitable low power circuitry can ensure functionality for as long as ten or more years, depending upon the operating temperatures and read/write cycles and usage. So-called passive RFID tags operate without a separate external power source and obtain operating power generated from the reader. Passive RFID tags are typically programmed with a unique set of data (usually 32 to 128 bits) that cannot be modified. Read-only tags may operate as an identifier comparable to linear barcodes which may contain selected product-specific information. Thus, passive RFID tags may be much lighter than active RFID tags, less expensive, and may offer a virtually unlimited operational lifetime. The tradeoff is that they have shorter read ranges than active tags and require a higher-powered reader.

One advantage of RFID approach is the noncontact, non-line-of-sight nature of the technology. Tags can be read through a variety of substances such as snow, fog, ice, paint, crusted grime, and other visually and environmentally challenging conditions, where other optically read technologies may be less effective. RFID tags can also be read in challenging circumstances at rapid speeds, in most cases responding in less than about 100 milliseconds.

While certain representative embodiments and details have been shown for purposes of illustrating aspects contemplated by the instant disclosure, it will be apparent to those skilled in the art that various changes in the methods and apparatus disclosed herein may be made without departing form the scope contemplated by the instant disclosure, which is defined in the appended claims. For example, other access port sizes and shapes may be employed; and various other embodiments and structures may be employed for forming at least one identifiable feature of an access port contemplated by the instant disclosure. In particular, FIGS. 25-51 illustrate a number of additional exemplary embodiments of access port 10. As is apparent from these figures, access port 10 may be formed in any number of shapes and sizes, such that any number of modifications and changes are possible to any of the embodiments described and illustrated herein without departing from the spirit and scope of the instant disclosure.

What is claimed is:

1. A venous access port assembly for implantation into a patient, comprising:
    a housing having a discharge port, a needle-penetrable septum, and a cap securable to the housing and retaining the septum securely in the assembly, the housing having a housing base defining a bottom wall of at least one reservoir, and an outwardly facing bottom surface,
    the housing base including radiopaque alphanumeric characters that convey to a practitioner that the venous access port assembly is power injectable when an X-ray of the patient is taken after implantation.

2. The assembly of claim 1, wherein the radiopaque alphanumeric message is applied to a surface of the housing base.

3. The assembly of claim 1 wherein the radiopaque alphanumeric message is applied to the outwardly facing bottom surface of the housing base.

4. The assembly of claim 1, wherein the radiopaque alphanumeric characters include the letters "C" and "T".

5. A venous access port assembly for implantation into a patient, comprising:
   a housing having an outlet, and
   a needle-penetrable septum, the needle-penetrable septum and the housing together defining a reservoir,
   wherein:
   the assembly includes a radiopaque alphanumeric message observable through interaction with X-rays subsequent to subcutaneous implantation of the assembly, and
   the alphanumeric message indicating that the assembly is power injectable.

6. The assembly of claim 5, wherein the alphanumeric message includes an abbreviation for computed tomography.

7. The assembly of claim 5, wherein the alphanumeric message is applied to the exterior of the assembly.

8. A venous access port assembly for implantation into a patient, comprising:
   a housing and a needle-penetrable septum together defining a reservoir; and
   the housing including an outlet and a radiopaque alphanumeric message observable through interaction with X-rays subsequent to subcutaneous implantation of the assembly into the patient, the radiopaque alphanumeric message identifying the venous access port assembly as suitable for power injection.

9. The assembly of claim 8, wherein the radiopaque alphanumeric message includes "C" and "T".

10. A venous access port assembly for implantation into a patient, comprising:
    a housing and a needle-penetrable septum together defining a reservoir; and
    the housing including radiopaque markings including the alphanumeric message "CT" that conveys to a practitioner when an X-ray of the patient is taken after implantation that the venous access port assembly is suitable for power injection.

* * * * *

UNITED STATES PATENT AND TRADEMARK OFFICE
CERTIFICATE OF CORRECTION

| | |
|---|---|
| PATENT NO. | : 7,785,302 B2 |
| APPLICATION NO. | : 11/368954 |
| DATED | : August 31, 2010 |
| INVENTOR(S) | : Kelly B. Powers et al. |

It is certified that error appears in the above-identified patent and that said Letters Patent is hereby corrected as shown below:

In the issued patent, Column 11, delete paragraph consisting of line numbers 15-40.

Signed and Sealed this
Nineteenth Day of July, 2011

David J. Kappos
*Director of the United States Patent and Trademark Office*